(12) United States Patent
Martin

(10) Patent No.: US 8,017,032 B2
(45) Date of Patent: *Sep. 13, 2011

(54) TABLET COMPOSITION FOR THE IN-SITU GENERATION OF CHLORINE DIOXIDE FOR USE IN ANTIMICROBIAL APPLICATIONS

(75) Inventor: Roy W. Martin, Downers Grove, IL (US)

(73) Assignee: Truox, Inc., McClellan, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/806,964

(22) Filed: Aug. 25, 2010

(65) Prior Publication Data

US 2010/0323009 A1    Dec. 23, 2010

Related U.S. Application Data

(63) Continuation-in-part of application No. 12/802,230, filed on Jun. 2, 2010, which is a continuation-in-part of application No. 12/660,470, filed on Feb. 25, 2010, which is a continuation-in-part of application No. 12/655,953, filed on Jan. 11, 2010, which is a continuation-in-part of application No. 12/653,984, filed on Dec. 22, 2009, which is a continuation-in-part of application No. 12/380,329, filed on Feb. 26, 2009, which is a continuation-in-part of application No. 11/253,977, filed on Oct. 18, 2005, now Pat. No. 7,534,368, which is a continuation-in-part of application No. 11/154,086, filed on Jun. 15, 2005, now Pat. No. 7,514,019, which is a continuation-in-part of application No. 11/070,132, filed on Mar. 1, 2005, now abandoned.

(51) Int. Cl.
*C01B 11/10* (2006.01)
*C01B 11/02* (2006.01)
*C11D 3/395* (2006.01)
*A01N 25/34* (2006.01)
*A61K 9/30* (2006.01)

(52) U.S. Cl. ......... 252/187.23; 252/187.21; 252/187.22; 252/187.33; 252/186.21; 252/186.25; 252/186.34; 252/186.35; 252/187.2; 252/186.36; 424/408; 424/475; 424/481; 424/482; 424/661

(58) Field of Classification Search ............ 252/186.21, 252/186.25, 186.36, 187.2, 187.21, 187.23, 252/187.34; 424/408, 475, 481, 661, 663
See application file for complete search history.

(56) References Cited

U.S. PATENT DOCUMENTS 2,815,311 A * 12/1957 Dvorkovitz et al. .......... 424/723
(Continued)

FOREIGN PATENT DOCUMENTS

WO    WO 2007/078838    7/2007

*Primary Examiner* — Joseph D Anthony

(57) ABSTRACT

A solid composition in the form of a tablet that generates and releases a biocidal solution comprising at least chlorine dioxide with an enhanced weight percent yield is presented. The composition comprises reactants capable of in-situ generation of chlorine dioxide comprising a chlorite donor that is coated with a gel-forming material that slows the rate of dissolution of the high solubility chlorite donor, a free halogen donor, and an acid source, resulting in an unexpectedly high weight percent yield and providing a controlled release of biocidal solution. The compositions of the invention show improved environmental stability which can reduce the cost of packaging and significantly increase the utility of the composition. The controlled release allows the use in multi-tablet chemical dispensers which may otherwise induce potentially explosive conditions or allow rapid release of the biocidal solution thereby inducing a spike in chemical concentration rather than a controlled and sustained release.

58 Claims, 6 Drawing Sheets

U.S. PATENT DOCUMENTS

| | | | |
|---|---|---|---|
| 3,671,629 A | 6/1972 | Levy et. al. | |
| 4,330,531 A * | 5/1982 | Alliger | 424/661 |
| 4,671,972 A | 6/1987 | Schobel et al. | |
| 5,525,121 A | 6/1996 | Heffner et al. | |
| 5,651,977 A * | 7/1997 | Kross | 424/419 |
| 5,651,996 A * | 7/1997 | Roozdar | 424/665 |
| 5,688,515 A | 11/1997 | Kuechler et al. | |
| 5,755,993 A | 5/1998 | Heffner et al. | |
| 5,801,116 A | 9/1998 | Cottrell et al. | |
| 5,965,264 A * | 10/1999 | Barenberg et al. | 428/402 |
| 6,039,934 A * | 3/2000 | Alliger | 424/53 |
| 6,132,748 A * | 10/2000 | Khanna et al. | 424/405 |
| 6,238,643 B1 * | 5/2001 | Thangaraj et al. | 423/477 |
| 6,277,408 B1 * | 8/2001 | Wellinghoff et al. | 424/473 |
| 6,319,888 B2 | 11/2001 | Wei et al. | |
| 6,384,006 B1 | 5/2002 | Wei et al. | |
| 6,569,353 B1 | 5/2003 | Giletto et al. | |
| 6,663,902 B1 * | 12/2003 | Hei et al. | 424/661 |
| 6,699,404 B2 | 3/2004 | Speronello et al. | |
| 7,150,854 B2 | 12/2006 | Koermer et al. | |
| 7,182,883 B2 | 2/2007 | Speronello et al. | |
| 7,204,931 B2 * | 4/2007 | Martin et al. | 210/755 |
| 7,465,410 B2 * | 12/2008 | Martin et al. | 252/186.25 |
| 7,514,019 B2 * | 4/2009 | Martin | 252/187.23 |
| 7,534,368 B2 * | 5/2009 | Martin | 252/187.23 |
| 7,666,384 B2 * | 2/2010 | Sanderson | 423/477 |
| 2001/0012504 A1 | 8/2001 | Thangaraj et al. | |
| 2002/0155067 A1 * | 10/2002 | MacGregor | 424/44 |
| 2003/0080317 A1 * | 5/2003 | Speronello et al. | 252/175 |
| 2003/0180384 A1 | 9/2003 | Koermer et al. | |
| 2005/0113279 A1 | 5/2005 | Desmarescaux et al. | |
| 2005/0155936 A1 * | 7/2005 | Martin et al. | 210/754 |
| 2006/0014872 A1 * | 1/2006 | Martin | 524/386 |
| 2006/0169949 A1 * | 8/2006 | Speronello et al. | 252/187.23 |
| 2006/0197058 A1 * | 9/2006 | Martin | 252/188.1 |
| 2007/0172412 A1 * | 7/2007 | Hratko et al. | 423/477 |
| 2008/0299161 A1 * | 12/2008 | Sanderson | 424/408 |

* cited by examiner

TABLET COMPOSITION FOR THE IN-SITU GENERATION OF CHLORINE DIOXIDE FOR USE IN ANTIMICROBIAL APPLICATIONS

RELATED APPLICATIONS

This application is a Continuation-in-Part (CIP) of U.S. patent application Ser. No. 12/802,230 filed on 2 Jun. 2010, which is a CIP of U.S. patent application Ser. No. 12/660,470 filed on 25 Feb. 2010, which is a CIP of U.S. patent application Ser. No. 12/655,953 filed on 11 Jan. 2010, which is a CIP of U.S. patent application Ser. No. 12/653,984 filed on 22 Dec. 2009, which is a CIP of U.S. patent application Ser. No. 12/380,329 filed on 26 Feb. 2009, which is a CIP of U.S. patent application Ser. No. 11/253,977 filed on 18 Oct. 2005, which is now U.S. Pat. No. 7,534,368, which is a CIP of U.S. patent application Ser. No. 11/154,086 filed on 15 Jun. 2005 which is now U.S. Pat. No. 7,514,019, which is a CIP of U.S. patent application Ser. No. 11/070,132 filed on 1 Mar. 2005 which is now Abandoned. The entire contents of these patent applications are incorporated by reference herein.

FIELD OF INVENTION

This invention relates to a solid composition in the form of a tablet that produces chlorine dioxide when contacted with an aqueous solution that is sufficiently stable for bulk packaging, provides a controlled release of at least chlorine dioxide, and is suitable for use in a multi-tablet chemical dispenser. The tablet of the invention provides at least a 20 weight percent yield of chlorine dioxide and allows in excess of 30 weight percent yield of chlorine dioxide. The weight percent yield achieved by a solid composition in the form of a tablet of the invention is unprecedented.

BACKGROUND

Oxidizing biocides are commonly used for the treatment of recirculating systems such as industrial cooling systems. It is common for tablet forms to be applied thru feeders such as flow through chlorinators or brominators. However, in many instances chlorine and bromine alone are not sufficient for the control of microbiological activity, especially in contaminated systems and/or where the pH is elevated which reduces the effectiveness of chlorine and bromine oxidizers.

Chlorine dioxide is an effective antimicrobial agent for use in food processing applications. Examples of food process applications include but are not limited to: vegetable and fruit washing, cleaning of animal processing equipment, cleaning of animal carcasses, treatment of poultry and animal habitats.

Chlorine dioxide has been shown to be very effective for the control of microbiological organisms. However, cost effective generation of chlorine dioxide requires on-sight generation from liquid reagents and substantial capital investment.

In recent years, tablets that generate chlorine dioxide have been developed, however their use in the treatment of recirculating systems is very limited due to high use cost and limited utility. High use cost is attributed to the tablet's low yields of chlorine dioxide and poor environmental stability that requires costly individual packaging of the tablets. Also, the high reactivity and rapid release of the chlorine dioxide results in a spike of treatment rather than the desirable controlled release to achieve a sustained concentration of treatment, and subsequent potential for generation of explosive conditions when applied in multi-tablet chemical dispensers due to elevated levels of potentially hazardous and explosive gas.

U.S. Pat. No. 6,699,404 to Speronello ("the Speronello patent") discloses a massive body having a porous structure which substantially increases the percent conversion of chlorite to chlorine dioxide when compared to chlorite powder. The Speronello patent discloses two types of massive bodies: a water soluble type and a substantially water insoluble type. The substantially water insoluble massive body forms a porous framework that provides a higher efficiency of the conversion compared to the water-soluble massive body. According to the test data provided in the Speronello patent the maximum concentration of chlorine dioxide produced by a massive body that forms the porous framework is 149.4 mg/L. The water-soluble massive body reported (example 4) a maximum 27.4 mg/L.

In order to achieve 70% or more conversion of the chlorite to chlorine dioxide using the method disclosed in the Speronello patent, a substantial amount of inert materials are added to produce the porous structure or the porous framework. The level of inert salts ranges from 18 wt. % to 80 wt. %, with higher weight percentages increasing the conversion efficiency. The high levels of inert material, particularly in the water-soluble massive body, are further illustrated in commercial practice. For example, Aseptrol®, which is the commercialized product embodying the invention disclosed in the Speronello patent, is a water soluble tablet that requires 1.5 grams of Aseptrol® to 1 liter of water to produce 100 mg/L chlorine dioxide. This equates to approximately 67 mg/L chlorine dioxide based on 1 gram tablet per liter. The weight-% yield, which is defined as weight of the chlorine dioxide divided by the weight of the tablet, is low because of the high level of inert material. According to the data reported in the Speronello patent, the weight % yield is less than 15 wt. %, and less than 3% in the case of the water-soluble massive body. Based on the commercial product Aseptrol®, the weight percent yield of the water soluble commercial product is 6.7 wt. %.

It is desirable to increase the concentration of chlorine dioxide produced by a given mass of tablet to improve the economics based on the cost per pound of the tablet material versus pounds of chlorine dioxide produced. Such increase would also result in an overall performance enhancement offered by higher concentrations of chlorine dioxide. To achieve this objective, tablet conversion efficiency of >70% and a high reactant weight percent are desirable. It is also desirable to substantially increase the concentration of chlorine dioxide using a completely water-soluble composition to eliminate the problems associated with water insoluble constituents or byproducts such as residue silica based clays, or mineral salts such as calcium sulfate.

U.S. Pat. Nos. 6,384,006 and 6,319,888 to Wei et al. ("the Wei patents") disclose a system for forming and releasing an aqueous peracid solution. The system includes a container and a peracid forming composition that includes about 10-60 wt. % of a chemical heater that, upon contact with water, generates heat to increase the yield of the peracid.

The Wei patents describe the potential use of a viscosity modifier within a permeable container to increase the viscosity in the localized area from about 300 to about 2,000 centipoise. The increased viscosity restricts and slows down the movement of peracid precursor and/or peroxygen source out of the permeable container. This results in an increased residence time of the peracid precursor and peroxygen source within the permeable container, which in turn translates to a greater reaction rate.

U.S. Pat. No. 6,569,353 to Giletto et al. ("the Giletto patent") discloses using silica gel to increase the viscosity of various oxidants including an in-situ generated oxidant in order to keep them in intimate contact with the agents targeted for oxidation.

U.S. Published Application No. 2001/0012504 to Thangaraj et al. ("the Thangaraj application") discloses a composition for producing chlorine dioxide comprising an acid source and a chlorite source, and a method comprising enclosing the composition in a gelatin capsule or membrane sheet such as a "tea bag".

U.S. Pat. No. 5,688,515 discloses a composition comprising trichloroisocyanuric acid, sodium bromide, and dimethylhydantoin to produce hypobromous acid.

Patent Application WO 2007/078838 discloses a composition comprising an oxidizer and bromide donor along with a chlorite donor to produce chlorine dioxide. The compositions disclosed generate chlorine dioxide rapidly and preferably without the use of chlorine donors such as chlorinated isocyanurates. The compositions also require special packaging to prevent chlorine dioxide generation resulting from relative humidity.

In order to improve reaction kinetics, the above references teach using substantial quantities of inert materials to either provide a porous structure as in the case of the Speronello patent, or heat as in the cases of the Wei patents. While viscosity modifiers are referenced in the Wei patents, the viscosity range disclosed in the Wei patents does not reflect the formation of a gel.

U.S. Pat. No. 7,514,019 B2 discloses a solvent-activated reactor including a gel layer that allows for a water-soluble tablet composition that delivers at least a 70 wt % conversion of chlorite to chlorine dioxide and at least 14 wt % yield. However, the maximum yield of chlorine dioxide achieved in the disclosed data was 18.1 weight percent.

U.S. Pat. No. 7,465,410 B2 discloses a solvent-activated reactor comprising a core of reactants that are encapsulated by a solvent-permeable reactor wall. The solvent activated reactor allows for a convenient means of generating a target product, however provides no improvements in weight percent yield or environmental stability than that disclosed in U.S. Pat. No. 7,514,019 B2.

U.S. Pat. No. 7,150,854 discloses a device comprising a substrate and reagents that permits the rapid release of relatively small quantities of chlorine dioxide in liquid water as needed and is therefore quite useful for sterilizing water such that it is potable and useful as a germicidal liquid. Furthermore, the present invention lends itself to the separation of the reaction precursors into discrete zones or domains, thereby resulting in increased shelf life and the avoidance of expensive packaging.

Search still continues for a method of stabilizing reactive components for storage without compromising or limiting their function during usage. Furthermore, it is highly desirable to have an environmentally stable tablet composition that provides an enhanced weight percent yield of chlorine dioxide that is at least 20 wt %, preferably 25 wt % and most preferably at least 30 wt %. Further still, the application of chlorine dioxide is severely limited due to poor environmental stability which lends itself to individually wrapped packaging, increased use cost, and lack of controlled release.

SUMMARY

It has been discovered that the weight percent yield of chlorine dioxide resulting from a solid composition in the form of a tablet is surprisingly and substantially increased to levels never before possible allowing at least 20 wt % yield, more preferably at least 25 wt % yield, and most desirably at least 30 wt % yield. Another benefit resulting from the disclosed invention is the dramatic improvements in environmental stability and the subsequent increased utility resulting from it such as bulk packaging and application of the composition in a multi-tablet dispenser. The invention provides for a tablet with enhanced weight percent yield of chlorine dioxide whether used alone or in combination with multiple tablets and a controlled release of chlorine dioxide that can be optimized by altering the gelling agent chemistry.

In one aspect, the invention is a solid composition in the form of a tablet with an enhanced weight percent yield that generates chlorine dioxide and releases an antimicrobial solution. The composition comprises reactants capable of generating the target product comprising at least chlorine dioxide through a chemical reaction, and a gel-forming material that allows for high yield and increased conversion of chlorite to chlorine dioxide. The chemical reaction is triggered when the reactants comprising the solid composition is contacted by an aqueous solution. The reactants include a free halogen donor, a chlorite donor, an acid source, and a gel-forming material that makes up about 0.1 to 30 weight % of the composition. All weight percents are based on the weight of the composition unless otherwise stated. The chlorite donor is coated or encapsulated with at least some portion of the gel-forming material. Upon being exposed to the main solvent, the gel-forming material swells forming a gelatinous structure that encapsulates the high solubility chlorite donor thereby slowing the dissolution rate of the chlorite, and creates a chamber within the composition enclosing some of the reactants such that the target product is generated in the chamber, wherein the gelatinous structure restricts diffusion of the reactants and the target product out of the chamber, restricts the diffusion of the main solvent into the chamber, and wherein the gelatinous structure dissipates when a depletion level is reached inside the chamber. Different parts of the composition are exposed to the main solvent at different times.

The gelatinous structure functions as a temporary membrane that restricts the diffusion of the main solvent (aqueous solution) to the chlorite thereby retaining chlorite in contact with the other reactants, restricts the dissolution of reactants, allows formation of in-situ generated chlorine dioxide by reaction between high concentrations of reactants thereby inducing high percentage of conversion of chlorite anion to chlorine dioxide, and restricts the dissolution of the chlorine dioxide into the bulk of the main solvent. As a result of this theorized mechanism, a high conversion of chlorite anion to chlorine dioxide occurs allowing at least 70 wt % conversion, more preferably 80% conversion and most preferred 90% conversion of chlorite anion to chlorine dioxide. Of great benefit and value is the ability of a solid composition in the form of a tablet to generate chlorine dioxide having a weight percent yield (wt % yield) of at least 20 wt %, and more preferably at least 25 wt % and most preferred at least 30 wt %.

In another aspect, the invention is a solid composition in the form of a tablet that generates chlorine dioxide and releases an antimicrobial solution for the treatment of food processing applications include but are not limited to: vegetable and fruit washing, cleaning of animal processing equipment, cleaning of animal carcasses, treatment of poultry and animal habitats. The tablet composition has substantial environmental stability.

In another aspect, the invention is a solid composition in the form of a tablet that generates chlorine dioxide and releases an antimicrobial solution for the treatment of recirculating systems including industrial cooling systems, swimming pools, spas, fountains, water parks; and hard surfaces such as those located in buildings and institutions such as hospitals, schools, office buildings, military bases and the like. The invention is also suitable for sanitizing surgical instruments and equipment exemplified by scalpels and endoscopes.

In another aspect, the invention is a solid composition in the form of a tablet that generates chlorine dioxide and releases an antimicrobial solution for the treatment of emergency drinking water. Emergency drinking water may be used by hikers, campers, survivalist, military, and emergency services such as FEMA.

In another aspect, the invention provides for solid composition in the form of a tablet capable of achieving conversion of chlorite anion to chlorine dioxide of at least 70 wt %, with a preferred conversion of least 80 wt %, and a most preferred conversion of at least 90 wt %. The conversion of chlorite anion to chlorine dioxide can be achieved using a substantially water soluble composition that provides at least 20 wt % yield of chlorine dioxide, more preferably the composition can be formulated to achieve at least 25 wt % yield of chlorine dioxide, and most preferably the composition can be formulated to achieve at least 30 wt % yield of chlorine dioxide.

In another aspect, the invention is a solid composition in the form of a tablet that has increased environmental stability. The proper selection and application of the gel-forming material can make the composition extremely stable until it is in intimate contact with an aqueous solution. Even when immersed in an aqueous solution, the said tablet can be made to have a delayed reaction because of the formation of a viscous film that restricts the water and movement of the dissolving reactants. It will be shown that this restriction can also result in a self-limiting tablet, such that the generation of chlorine dioxide can be made to substantially slow or stop when the weight ratio of the tablet to water gets too high. It is believed the increasing viscosity elevates the concentration of the reactants to where they reach their saturation level and the tablet slows its dissolution rate.

In another aspect, the invention is a composition that releases at least chlorine dioxide at a controlled rate thereby providing an antimicrobial solution for an extended period of time and allowing use in multi-tablet chemical dispensers. Tablets can be designed to release the antimicrobial solution over minutes, hours or days instead of a rapid release of chlorine dioxide like compositions disclosed in the reference prior art, which in an enclosed compartment of a chemical dispenser can produce potentially catastrophic conditions. The ability to customize the release rate of chlorine dioxide expands the utility of the solid compositions of the invention. Tablets can be made to generate a high wt % yield of chlorine dioxide quickly by applying a single or multiple tablets to a volume of water to produce an antimicrobial solution for disinfecting surfaces. In another example, a plurality of tablets can be added to a multi-tablet dispenser that serves to produce an antimicrobial solution and apply said solution to a recirculating system such as a cooling system for an extended period of time. The ability to alter the gel chemistry of the tablet greatly expands the safety and utility of the tablets.

In another aspect, the invention is a method of producing a composition that generates chlorine dioxide with enhanced weight percent yield and environmental stability. The method entails coating the chlorite donor with a gel-forming material comprising a polymer, more preferably and synthetic polymer that is a oxidation resistant polymer. The gel-forming material slows the dissolution of the high solubility chlorite. The reactants of the composition are combined, mixed and agglomerated into a tablet composition. When the tablet composition is immersed in water, the coated chlorite forms a viscous gel at the surface of the high solubility chlorite, thereby restricting its dissolution. The gel from a plurality of polymer coated chlorite interconnect and form chambers that entrap the other reactants in the composition thereby enhances the contact time between the free halogen donor exemplified by trichloroisocyanuric acid and acid source exemplified by fumaric acid. The gel forms a temporary membrane that functions as a reactor by keeping the reactants in intimate contact until a high conversion of chlorite anions to chlorine dioxide takes place. It is also desirable, but not required to use a low solubility acid source such as fumaric acid.

In yet another aspect, by combining low solubility free halogen donor with the encapsulated chlorite donor that has a restricted dissolution rate results in unexpected dramatic increases in the tablet stability and weight percent yield that exceed 25 wt % and most preferred exceeds 30 wt %.

The resulting tablets composition has improved environmental stability and can be made suitable for bulk packaging. Current tablets that generate relatively low weight percent yield of chlorine dioxide are packaged as individual tablets to protect from relative humidity and premature release of chlorine dioxide. The tablets of the invention are sufficiently stable as to make them suitable for bulk packaging wherein multiple tablets are provided in one package. This substantially reduces cost and increases utility.

In another aspect, the invention is a water soluble tablet composition that is non-hygroscopic and generates chlorine dioxide with a weight % yield of at least 20 wt % and a chlorite conversion of at least 70 wt %.

In yet another aspect, the invention allows for the tablets to be used in a multi-tablet dispenser for on-site generation of antimicrobial solution.

DETAILED DESCRIPTION OF THE EMBODIMENT(S)

Figure 1:
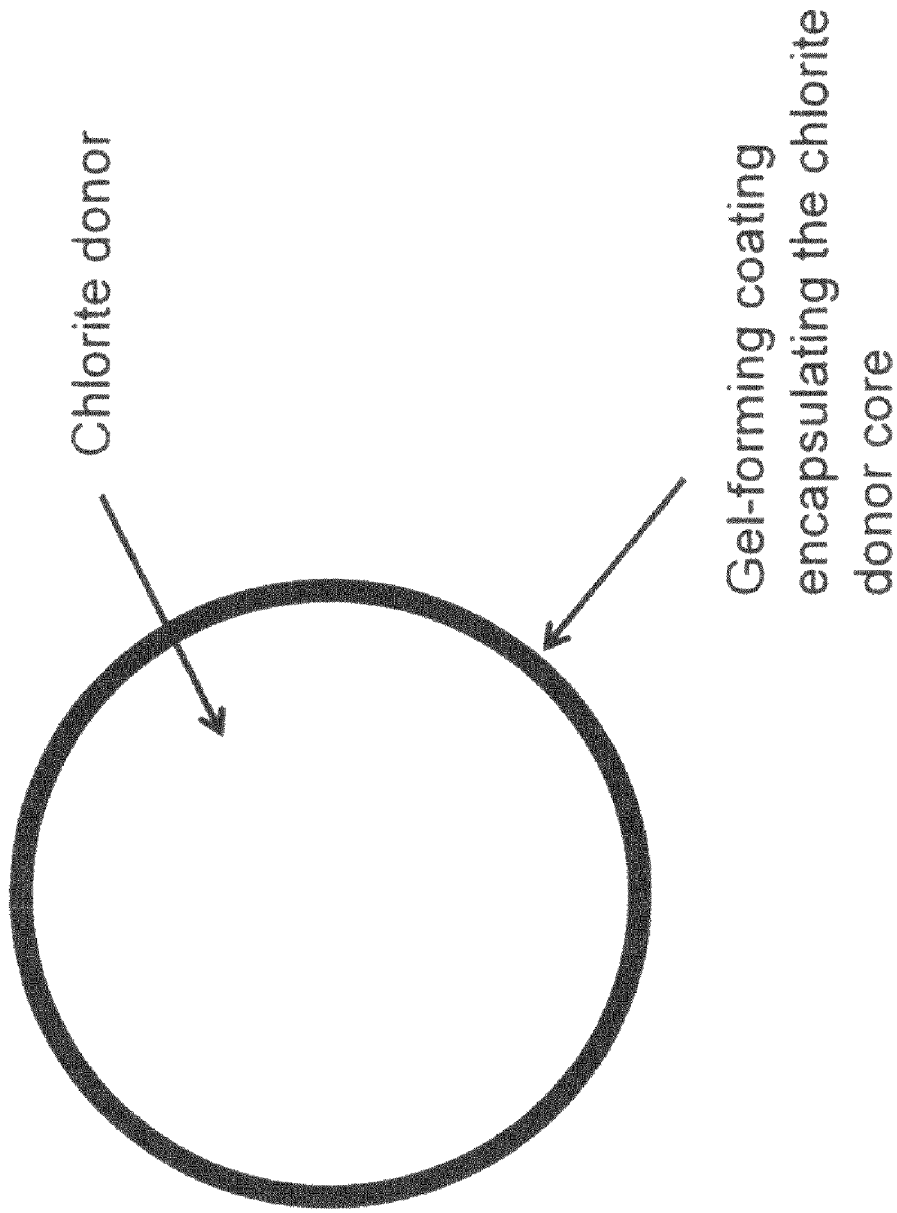
FIG. 1 is an exemplary embodiment of reactor in accordance with the invention.

The invention is particularly applicable to generation and release of chlorine dioxide having bleaching, biocidal, or virucidal properties and it is in this context that the invention will be described. It will be appreciated, however, that the reactor, the method of making the reactor, and the method of using the reactor in accordance with the invention has greater utility and may be used for any other target product(s). Although the main solvent is described as water for clarity of illustration, the invention is not so limited.

As used herein "enhanced weight percent yield" defines a tablet composition that generates chlorine dioxide equivalent to at least 20 wt % of the total tablet weight when immersed in water. The enhanced weight percent yield can be achieved even in very dilute solutions comprising less than 0.02 wt % of tablet composition (e.g. a 1.5 gram tablet to 8 liters of water).

As used herein "food processing applications" include those aspects within the process that utilize antimicrobial treatments to reduce the potential of spread of infectious disease. Applications include: vegetable and fruit washing; cleaning and sanitizing of food processing equipment; cleaning and sanitizing of animal carcasses, poultry, meat, rabbit, and egg products, treatment of poultry and animal habitats.

As used herein, "carboxylic acid donor" describes dicarboxylic acid and tricarboxylic acid that have a molecular weight between 90 and 300 grams per mole. Examples include succinic acid, malonic acid, maleic acid, malic acid, tartaric acid, fumaric acid, glutaric acid, and citric acid. Of these, fumaric acid exemplifies a preferred polycarboxylic acid due to its non-hygroscopic properties.

As used herein, "acid source" describes compounds that contribute hydrogen ions ($H^+$) when dissolved in water. Examples of inorganic acid sources include but are not limited to sodium bisulfate, potassium bisulfate, sodium pyrosulfate, and potassium pyrosulfate. Organic based acid sources include but are not limited to fumaric acid, succinic acid and citric acid.

As used herein, "non-hygroscopic" describes the tablet composition comprising the free halogen donor, acid source and chlorite donor that resist adsorption or absorption of moisture when exposed to atmospheric humidity thereby substantially reducing the potential for the generation of chlorine dioxide. The non-hygroscopic property of the tablet composition can be achieved by: coating the hygroscopic components of the tablet composition with a film forming material exemplified by polyvinyl alcohol; coating the said hygroscopic components with a non-hygroscopic material exemplified by magnesium carbonate light or fumed silica; and/or coating the hygroscopic components with a non-hygroscopic components exemplified by coating the sodium chlorite with non-hygroscopic fumaric acid which is used in the generation of chlorine dioxide.

As used herein, "effective amount of combustion suppressing boron donor" defines an effective amount of boron containing compound exemplified by borax and boric acid that can reduce the combustion rate of the solid composition to a packing group having lower transportation and/or storage restrictions. Division 5.1 Oxidizer Testing in accordance with the *Code of Federal Regulations, Title 49, and the United Nations Transportation of Dangerous Goods-Manual of Test and Criteria, Fourth revised edition* (2003). Solid Division 5.1 materials are assigned packing groups using the following criteria [49 CFR .sctn.173.127(b)]: (i) Packing Group I is the sub-classification of any material which, in the 4:1 or 1:1 sample to cellulose ratio (by mass) tested exhibits a mean burning time less than the mean burning time of a 3:2 mixture, by mass, of potassium bromate and cellulose. (ii) Packing Group II is the sub-classification of any material which, in the 4:1 or 1:1 sample to cellulose ratio (by mass) tested exhibits a mean burning time less than the mean burning time of a 2:3 mixture, by mass, of potassium bromate and cellulose, and the criteria for Packing Group I are not met. (iii) Packing Group III is the sub-classification of any material which, in the 4:1 or 1:1 sample to cellulose ratio (by mass) tested exhibits a mean burning time less than the mean burning time of a 3:7 mixture, by mass, of potassium bromate and cellulose, and the criteria for Packing Groups I and II are not met.

The addition of an "effective amount of combustion suppressing boron donor" to the solid composition reduces the combustion rate of the solid composition resulting in a reducing the transportation and storage restrictions.

"Reaction chamber" is a space that is defined by the outline of a colloidal gel wall, and includes the enclosed by the colloidal gel, the colloidal gel itself, and any pores or channels in the colloidal gel. A "main solvent," is any solvent that dissolves the reactant(s) and triggers a chemical reaction. A "polymer," as used herein, includes a copolymer. A substance that is transported at a "controlled rate" does not cross a physical boundary explosively all at once but gradually, over a desired period of time.

As used herein, "depletion level" indicates a predetermined concentration level of the reactant(s) and the target product in a reaction chamber. When a reaction chamber is contacted by the main solvent, a chemical reaction is triggered and the reactant(s) in the reaction chamber are converted to the desired target product. The target product then leaves the reactor chamber at a controlled rate. The depletion level may be defined by parameters other than reactant concentration that also indicate the rate of target product generation, such as the pH level or the concentrations of the target product or a byproduct.

When the reactor wall "disintegrates," it could collapse due to a pressure difference between the inside and the outside of the reactor, dissolve in the main solvent, or come apart and dissipate due to forces applied by the movement in the main solvent. A membrane is a porous material that allows permeation of the solvent and diffusion of the product. "Water," as used herein, is not limited to pure water but can be an aqueous solution. A gelatinous structure "dissipates" by dissolving or dispersing in the main solvent.

"Gel," "hydrogel," and its various derivations (i.e. gelatinous) describes a material or combination of materials that undergo a high degree of cross-linking or association when hydrated and dispersed in the dispersing medium (e.g. aqueous solution), or when dissolved in the dispersing medium. This cross-linking or association of the dispersed phase will alter the viscosity of the dispersing medium to a level which restricts the movement of the dispersing medium. As used herein, "suspension" refers to a two-phase system consisting of a finely divided solid dispersed (suspended) in a liquid (the dispersing medium). Gels contain suspended particles but are different from suspensions in that these suspended particles create a three-dimensional structure of interlacing particles or solvated macromolecules that restrict the movement of the dispersing medium.

A "gel-forming material" is comprised of at least one gel-forming polymer that, upon contact with an aqueous solution, produces a gel, hydrocolloid or hydrogel. The polymer can be natural, such as a gum (e.g. Xanthun gum), semisynthetic such as a polysaccharide (e.g. cellulose derivative), or synthetic such as a poloxamer (block co-polymer of polyoxyethylene and polyoxypropylene), carbomer (crosslinked polymer of acrylic acid), poly (ethylene oxide) and polyvinyl alcohol. The gel-forming material may also include other additives that increase the viscosity or the gel. One example is borate exemplified by disodium octaborate.

A "stiffening agent" can be water-soluble or substantially water-insoluble. When combined with a gel-forming material, the stiffening agent substantially reduces the dissolution rate of the tablet composition. Stiffening agents can act as a cross-linking agent. An example of a stiffening agent is polyethylene wax exemplified by Luwax sold by BASF. Borax or boric acid that is converted to borate in-situ will increase the viscosity of polyvinyl alcohol and slow the dissolution rate of the tablet composition.

A "stiffening agent comprising boron" can be any source of boron containing compound that cross-links with polyvinyl alcohol under the conditions achieved within the gelatinous structure. Examples include but are not limited to: boric acid, borate in its varying hydrated forms and mixtures. Boric acid that reacts with hydroxide alkalinity released from the commercial sodium chlorite and released from the generation of chlorine dioxide converts boric acid to borate which then cross-links with the polyvinyl alcohol.

A "gelatinous structure" comprises the three-dimensional hydrocolloid or hydrogel produced by the hydrolysis of the gelling agent, which may include at least one natural, semi-synthetic, and synthetic polymer, as well as any reactants or products restrained or trapped by the three-dimensional hydrogel. The gelatinous structure describes a region defined by the coalesced gelatinous composition which forms the 3-dimensional structure. The regional boundaries are generally defined by the innermost portion of the gelatinous composition (approaching the surface of the remaining solid tablet) to the outermost boundary of the gelatinous composition (interfacing with the bulk of the dispersing medium). The gelatinous structure may have a viscosity gradient across the region.

A "gelling agent" defines the components required to produce the gelatinous structure. The gelling agent includes at least the gel-forming material. However the gelling agent may also include a stiffening agent, pH buffer, etc.

As used herein, the term "controlled release" refers to the solid composition in the form of a tablet, having been contacted with water, produces and releases chlorine dioxide over an extended period of time as opposed to a rapid release, and where the extended period of time can be measured in seconds, minutes, hours or days depending on the size of the tablet and amount of gel-forming material &/or gelling agent included in the tablet. A tablet with equivalent amounts of reactants under identical test conditions without gel-forming material will dissipate in the water in less time than the tablet that includes the gel-forming material. The chemistry of the gelling agent used in the composition can be adjusted to control the time required to generate and release the chlorine dioxide.

As used herein, the term "tablet" refers to any geometric shape or size that comprises the components necessary to produce a solution consisting of at least chlorine dioxide, and wherein the components are gathered together to form a single mass.

As used herein, the term "halogenated cyanuric acid" refers to any combination of chlorinated or chlorinated and brominated cyanuric acid compounds. Examples include but are not limited to trichloroisocyanurate, bromochloroisocyanurate.

As used herein, the term "slow dissolving" refers to the tablet of the invention having a restricted rate of dissolution compared to the rate of dissolution achieved from a tablet of similar composition that does not comprise a gelling agent. The gelling agent restricts the dissolution of the reactants thereby slowing the rate at which the tablet dissolves, and allows for a sustained release of in-situ generated products rather than a rapid release obtained by fast dissolving masses and powders.

As used herein, the term "free halogen donor" describes a source of free halogen that when dissolved in an aqueous solution contributes at least one of $Cl_2$, HOCl, $OCl^-$, $Br_2$, HOBr, $OBr^-$ the species of which is dependent on the solution pH and the source of free halogen donor. Example sources of free halogen donors include but are not limited to chlorinated cyanuric acid, chlorinated and brominated cyanuric acid, and brominated and/or chlorinated hydantoin. Examples include but are not limited to: trichloroisocyanurate, dichloroisocyanurate, potassium chlorobromoisocyanurate, dibromodimethylhydantoin, bromochlorodimethylhydantoin, dichlorodimethylhydantoin.

As used herein, the term "free halogen" refers to free chlorine comprising any combination or proportion of chlorine gas, hypochlorous acid and hypochlorite ions and/or free bromine comprising any combination of bromine gas, hypobromous acid and hypobromite ions.

As used herein, the term "low solubility free halogen donor" refers to a free halogen donor having a solubility of no greater than 5 grams per 100 ml of water at 25° C. Examples include but may not be limited to trichloroisocyanuric acid, dichlorohydantoin, dibromodimethylhydantoin, bromochlorodimethylhydantoin, and the like.

As used herein, the term "multi-tablet chemical dispenser" describes any convenient feed system that holds multiple tablets of the invention and contacts at least some portion of the tablets with an aqueous solution to produce a solution consisting of at least chlorine dioxide. Examples include flow-thru brominators such as those sold by Great Lakes Water Treatment, Nalco Chemical, and BetzDearborn Inc. whose disperser is exemplified in U.S. Pat. No. 5,620,671, spray feeders like those sold by Arch Chemical and sold under the trade name Pulsar, floating dispensers, or a perforated dispenser such as a minnow bucket or strainer that is immersed into the aqueous solution.

As used herein, the term "enhanced environmental stability" is defined by the solid composition's ability to substantially resist the generation and release of chlorine dioxide until such time that it is exposed to an aqueous solution. A solid composition with enhanced environmental stability substantially reduces the potential of generation and release of chlorine dioxide when exposed to relative humidity such as that experienced during production, packaging, storage and handling.

As used herein, the term "bulk packaging" defines the ability to package a plurality of tablets into one package without segregating each tablet. Example packaging includes but is not limited to plastic bags and/or plastic pails. Bulk packaging requires the tablet possess sufficient environmental and chemical stability as to substantially eliminate the potential for formation of chlorine dioxide during packaging, storage and transport.

As used herein, the term "coated" refers to the application of the gel-forming material or gelling agent onto the surface of a reactant such as the chlorite donor. Coated also includes encapsulation of the reactant by the gel-forming material or gelling agent by application to the surface of the reactant using a means of spray coating, exemplified by, but not limited to the Wurster process of spray coating. Another method of encapsulating the chlorite or other reactants using a dry method of application of the gel-forming material is a process called Magnetic Assisted Impact Coating (MAIC), or by simply applying a coating in the form of a powder of gel-forming material that forms a gel membrane when contacted with an aqueous solution. The gel-forming material may also be applied onto the surface of the sodium chlorite then dried. A rotary drum drier fitted with a spraying device is suitable, however any number of spraying drying techniques can be employed.

As used herein, the term "surrounds" refers to the free halogen donor's position in relation to the in-situ generating portion of the composition. Surrounds includes encapsulates, sandwiches as in the case of two layers of free halogen donor with the in-situ generating portion between the two free halogen layers.

As used herein, the term "chlorite donor" is a substance that contributes chlorite anions having the formula $ClO_2^-$ when dissolved in an aqueous solution. The chlorite donor will generate chlorine dioxide when reacted with hypochlorous acid and/or hypobromous acid. Example of suitable chlorite donors include but are not limited to is sodium chlorite, magnesium chlorite, calcium chlorite as well as other alkali metals chlorite salts.

As used herein, the phrase "chlorite conversion to chlorine dioxide" describes the amount of chlorite anion having the general formula $ClO_2^-$ into the in-situ generated product chlorine dioxide having the general formula $ClO_2$. The amount of conversion is reported in weight percent (wt %) and is determined by dividing the amount (weight) of chlorine dioxide produced by the total amount of chlorite anion (weight) provided by the composition. The equation is represented by $ClO_2/ClO_2^- \times 100$=weight %

As used herein, the term "recirculating systems" describes any open aqueous system that consist of a reservoir of water and a system of piping to transport the water, and wherein the water transported through the piping is eventually returned to the reservoir. Examples of recirculating systems include but are not limited to: cooling systems such as cooling towers and cooling ponds, swimming pools, fountains and feature pools.

As used herein, the term "biocidal solution" describes an aqueous solution consisting of at least chlorine dioxide and results from contacting an aqueous solution with the slow dissolving tablet composition of the invention.

As used herein, the term "oxidation resistant polymer" describes a polymer possessing steric hindrance and bond strength resulting in increased resistance to oxidation from the oxidizers in the tablet composition. An oxidation resistant polymer is capable of being combined with sodium chlorite at the ratios used in the tablet composition and tested using thermogravimetric analyses (TGA) to a temperature of at least up to 100° C. without inducing a reaction between the sodium chlorite and said polymer. One example of an oxidation resistant polymer includes but is not limited to polyvinyl alcohol.

As used herein, the term "self-limiting" tablet composition describes the tablet composition's ability to slow or stop the generation of chlorine dioxide as the concentration of the tablet components and chlorine dioxide in the biocidal solution gets too high. Without being held to a particular theory, it is believed the increasing viscosity elevates the concentration of the reactants to where they reach their saturation level and the tablet slows its dissolution rate.

As used herein, the term "water" includes aqueous solution(s) that comprise water, but is not limited to strictly water having the general formula $H_2O$, wherein "H" is Hydrogen and "O" is Oxygen. The use of the term "water" is not meant to imply limitations to the use of the disclosed solid composition with respect to the quality of the water in an aqueous solution. An aqueous solution may contain contaminants, minerals, dissolved and suspended solids.

As used herein, the term "carboxylic acid" describes a an acid source having at least two carboxylic acid functional groups having the general formula COOH, wherein "C" is carbon, "O" is oxygen, and "H" is hydrogen.

The invention is based on the discovery that a solid tablet composition can be produced to provide an enhanced weight percent (wt %) yield of chlorine dioxide. The enhanced weight percent yield is obtained by combining select reactants that provide an optimum chemistry for generating chlorine dioxide with a gel-forming material comprising at least one of a natural, semi-synthetic and synthetic polymer that encapsulates the high solubility chlorite donor, and entraps the reactants within a gel matrix that functions as a membrane.

When the selective reactants are first exposed to a small volume of water and allowed to react to generate the target product, a high yield of the target product can be obtained because the reactant concentrations are high and the chemistry supports efficient conversion of chlorite anions to chlorine dioxide. Then, the chlorine dioxide can be exposed to a larger volume of water. The rate at which the reactants are exposed to water has to be such that the chlorine dioxide is generated in high yield before more water dilutes the reactants. The invention controls the dissolution of the reactants' upon exposure to water by forming a gel layer that functions as a temporary coating that keeps the reactants in intimate contact for a sufficient time period to allow the reactions to proceed toward completion. It is believed by coating at least the high solubility chlorite donor, the chlorite anions resulting from dissolution in water are restricted from dissipating away from the tablet and other reactants. The coating of the high solubility chlorite allows for addition of high amounts of chlorite donor into the solid composition which then effectively induces formation of a gel matrix across the wetted surfaces of the tablet thereby entrapping other reactants. Additional gel-forming material can be added to the solid composition which can be especially useful when using lower amounts of coated chlorite donor and/or using other high solubility reactants that would otherwise quickly dissipate and disperse.

Thus far, the oxidizing power of chlorine dioxide has not been fully exploited because the cost of equipment to produce chlorine dioxide in-situ to the application is prohibitively high. Also, when using conventional powders or tablets, the economics are severely compromised due to poor "weight % yield" of the powders and tablets as well as the cost of producing these chlorine dioxide generators. The poor "weight % yield" is demonstrated in the '404 Patent discussed above. Furthermore, the utility of chlorine dioxide tablets is compromised due to the poor environmental stability which results in individually wrapped tablets.

The ability to produce a tablet composition that: generates a high weight % yield of chlorine dioxide; has substantially improved environmental stability so that it can be packed in bulk wherein multiple tablets can be combined into one package rather than individually wrapped; have a controlled release rate when immersed in water to provide chlorine dioxide over an extended period of time; and be self-limiting so that the dissolution rate of the tablet composition substantially slows or stops as the concentration of the tablet composition components in the biocidal solution is substantially elevated, provides a tablet composition that eliminates the existing barriers for use of chlorine dioxide in multi-tablet dispensers.

Chlorine Dioxide

In one embodiment, the composition comprises: a chlorite donor exemplified by sodium chlorite having from approximately 34-69 wt % as commercial sodium chlorite based on having an 82 wt % sodium chlorite activity (approximately 20.6-42.0 wt % as chlorite anion); a free halogen donor exemplified by trichloroisocyanurate (TCCA) and ranging from 12-60 wt %, and in sufficient amount to convert at least 70 wt % of the chlorite anion to chlorine dioxide; an acid source comprising from 3-50 wt %, and in sufficient amount to provide a pH of less than 7.8 when 1 gram of tablet composition is dissolved in 100 ml of water; a gelling agent comprising from 0.1 wt % to 30 wt % of a gel-forming material comprising at least one of a natural, semi-synthetic, and synthetic polymer.

Without intent to limit the sources and types of gel-forming material, examples include polyvinyl alcohol sold under the trade name Elvanol® by DuPont, poly (ethylene oxide) sold under the trade name Polyox® by Dow Chemical, Poloxamer sold under the trade name Pluronic® by BASF, Carbomer sold under the trade name Carbopol® by Noveon, polysaccharides exemplified by Xanthan gum sold by Ingredient Solutions, Inc., and water soluble cellulose derivatives sold by Eastman. These examples comprise natural, semi-synthetic and synthetic polymers that increase the viscosity when contacted with an aqueous solution. The preferred gel-forming material is an oxidation resistant polymer exemplified by polyvinyl alcohol. The gelling agent may include a cross-linking agent exemplified by borax in the case of polyvinyl alcohol, a stiffening agent exemplified by polyethylene wax, or can be used alone. The composition provides a controlled release solid composition in the form of a tablet for use in multi-tablet dispensers and provides a conversion of chlorite anions to chlorine dioxide of at least 70 wt %. The use of the gelling agent also allows for sufficient chlorite donor to generate a yield of chlorine dioxide of at least 20 weight % while providing a substantially water soluble composition. A weight % yield of at least 30% has been achieved from tablets of this invention.

The preferred chlorite donor is sodium chlorite. However other chlorite donors that provide chlorite anions ($ClO_2^-$) when dissolved in water could be used in the composition.

Free halogen donors contribute halogen based oxidizers when contacted with an aqueous solution. For example, Trichloroisocyanuric acid (TCCA) releases free chlorine as it is dissolved by water. The species of the free chlorine is dependent on the pH of the solution. The species of free chlorine can include $Cl_2$, $HOCl$, and $OCl^-$. The species of free bromine can include $Br_2$, $HOBr$, and $OBr^-$.

An acid donor consumes the hydroxide alkalinity released from the formation of chlorine dioxide and released from the chlorite donor. The pH of the resulting biocidal solution was illustrated in the example test of the referenced co-pending applications. Acid sources can be organic and inorganic. Examples of organic acid sources include but are not limited to cyanuric acid, succinic acid, fumaric acid, tartaric acid, and citric acid. The preferred acid source is a dicarboxylic or tricarboxylic acid exemplified by fumaric acid and citric acid respectively. Fumaric acid is an example of a preferred organic acid having limited solubility and being substantially non-hygroscopic. Examples of inorganic acid sources include but are not limited to sodium bisulfate potassium bisulfate, sodium pyrosulfate and the like.

The gelling agent will be comprised of at least a polymer that, upon contact with an aqueous solution is capable of producing a hydrogel. The polymer can be natural, such as a gum (i.e. Xanthun gum), semisynthetic such as a polysaccharide (i.e. cellulose derivative), or synthetic such as a poloxamer, carbomer, poly (ethylene oxide), polyvinyl alcohol and the like. The preferred polymer is an oxidation resistant polymer that is exemplified by polyvinyl alcohol and carbomer. Oxidation resistant polymers such as polymers with cross-linking exemplified by polyvinyl alcohol and Carbomers reduce the potential for reacting with the reactants or the biocidal solution produced. Additional stiffening agents such as incorporating borax with polyvinyl alcohol can be used to increase the viscosity and further reduce dissolution rates of the reactants.

Additional additives such as pH buffers maybe included depending on the reactants used as well as the final application. For example in cases where trichloroisocyanuric acid (TCCA) is included, the acidity from the TCCA may be sufficient to neutralize the alkalinity from the chlorite donor. However, in applications where dibromodimethyl hydantoin (DBDMH) is used, additional acidity maybe required since DBDMH has a pH near neutral.

Optional Components in the Reactor
1) Fillers

Fillers can be used or altogether omitted depending on the type of processing and the requirements of the use of the final product. Fillers maybe inorganic compounds such as various mineral salts, metal oxides, zeolites, clays, aluminates, aluminum sulfate, polyaluminum chloride, polyacrylamide, and the like.

2) pH Buffers

A pH buffer provides a source of pH control within the reactor. The pH buffers can be inorganic (e.g. sodium bisulfate, sodium pyrosulfate, mono-, di-, tri-sodium phosphate, polyphosphates, sodium bicarbonate, sodium carbonate, boric acid, borax, and the like). Organic buffers are generally organic acids with 1-10 carbons such as succinic acid.

The pH buffer can be employed to adjust the pH of the solution resulting from the dissolution and reactions resulting from the composition in order to achieve the desired conversion of chlorite to chlorine dioxide and/or achieve the desired viscosity of the gel.

3) Cross-Linking Agents

Cross-linking agents, which are additives that change the physical or chemical properties of the composition, may be added to the reactor to control (e.g., reduce) the dissolution rate of the composition. For example, glycoluril is effective at bonding with hydroxyl and carboxylic acid groups such as those found in the cellulose of hydrolysed silicates. Glycerin and borates alter the water permeation rate of polyvinyl alcohol. Therefore, these types of agents can be added or left out depending on the final dissolution rate, hygroscopicity, chemical resistance to oxidizers, etc.

A cross-linking agent is mixed with the binder, and the mixture is combined with the reactants in the manner described above. In cases where curing is required to set the cross-linking agent, the binder and the cross-linking agent are combined in the presence of a solvent and/or a curing agent, mixed, and reacted. If needed the mixture is dried prior to application (e.g., being combined with the reactants).

4) Stiffening Agent

The stiffening agent is used to increase the viscosity of the gel and further slow the dissolution rate of the tablet. Polyethylene wax such as Luwax® sold by BASF is an example of a stiffening agent that further slows the dissolution of the tablet. Many hydrocarbon based polymers with low solubility or considered insoluble in water will serve as a stiffening agent. Cross-linking agents can also function to stiffen the gel as a result of increasing the gel viscosity and thereby reducing the dissolution rate of the tablet.

5) Surfactants

In some instances surfactants can be incorporated into the composition to reduce the dissolution rates of the higher solubility reactants as well as provide a synergistic effect in combination with the biocidal solution. For example, a block copolymer surfactant exemplified by Pluronic® manufactured by BASF can reduce the dissolution rate of the reactants as well as provide surfactant to the biocidal solution to enhance the performance of the chlorine dioxide by increasing the penetration of biofilms and membranes of microbiological organisms. Other examples include poly (ethylene oxide) sold by Dow Chemical under the name Polyox.

6) Other Additives

Other additive such as lubricants and potentially binders can be added to enhance the manufacturing of the tablet.

7) Anti-Caking Agents

It may be advantageous to apply an anti-caking agent exemplified by magnesium carbonate light, untreated fumed silica and treated fumed silica. Fumed silica is sold under the trade name CAB-O-SIL® and is manufactured by Cabot Corporation. Anti-caking agents can also reduce the hygroscopic nature of sodium chlorite as well as the entire solid composition.

A. Structure

FIG. 1 is an exemplary embodiment of the chlorite donor coated with a gel-forming material that encapsulates the chlorite donor.

Figure 2:
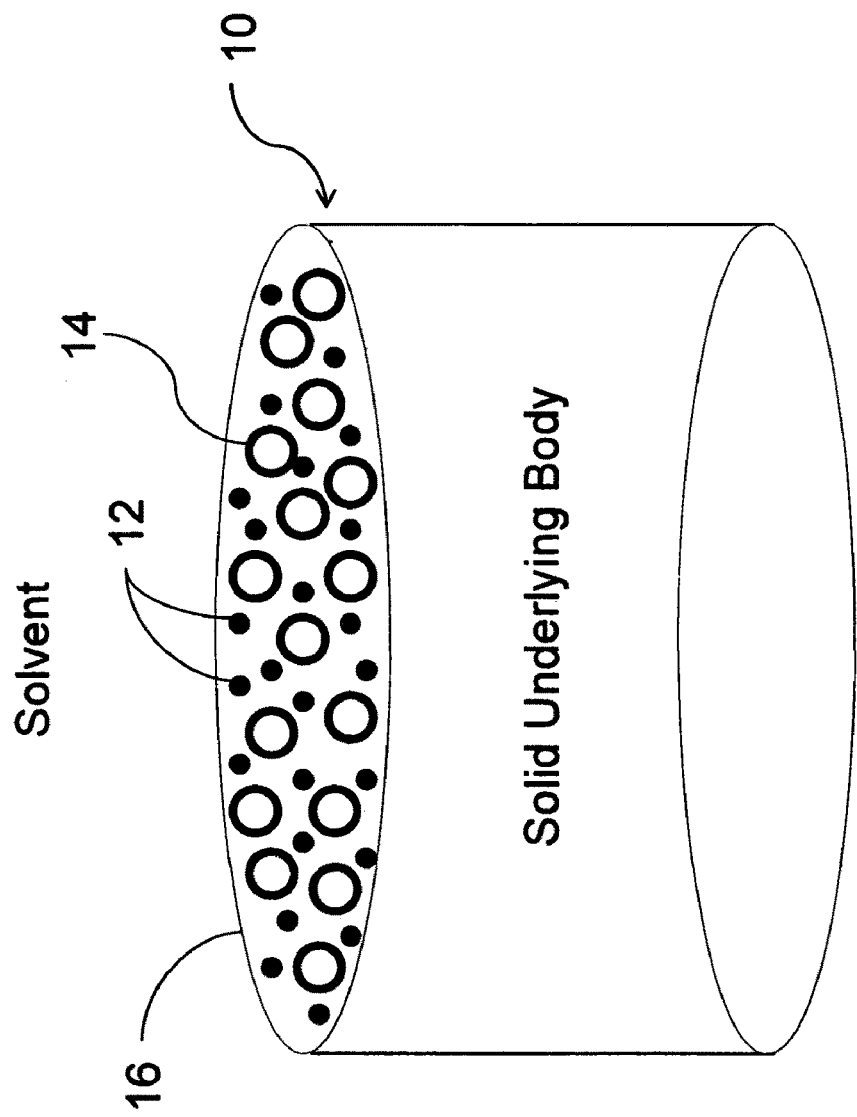
FIG. 2 is the reactor of FIG. 1 after the solvent interface has been exposed to the main solvent.

FIG. 2 is an exemplary embodiment of reactor 10 in accordance with an embodiment of the invention. Although the reactor 10 in this exemplary embodiment is cylindrically shaped, the invention is not so limited. The reactor 10 is an aggregate composition containing one or more reactants 12 and a chlorite donor encapsulated with a gel-forming material 14. Although the reactants 12 and the chlorite donor encapsulated with a gel-forming material are shown only for a solvent interface 16 of the reactor 10, they are preferably present throughout the reactor 10. The gel-forming material of 14 forms a gel when it comes in contact with the main solvent. Thus, when the reactor 10 is placed in contact with the main solvent, the gelling agent in the parts of the reactor 10 that come in contact with the main solvent will form a viscous gel that entraps the reactants 12, and divide the wet parts of the reactor 10 into multiple reactor chambers. The gel functions as a membrane allowing some permeation of the main solvent and other fluids across it, but in a restricted manner. Although only one interface 16 is shown in this example for simplicity of illustration, there may be multiple interfaces between the reactor 10 and the main solvent; in fact, the reactor 10 may be placed in a bulk body of main solvent resulting in its complete immersion.

Figure 3:
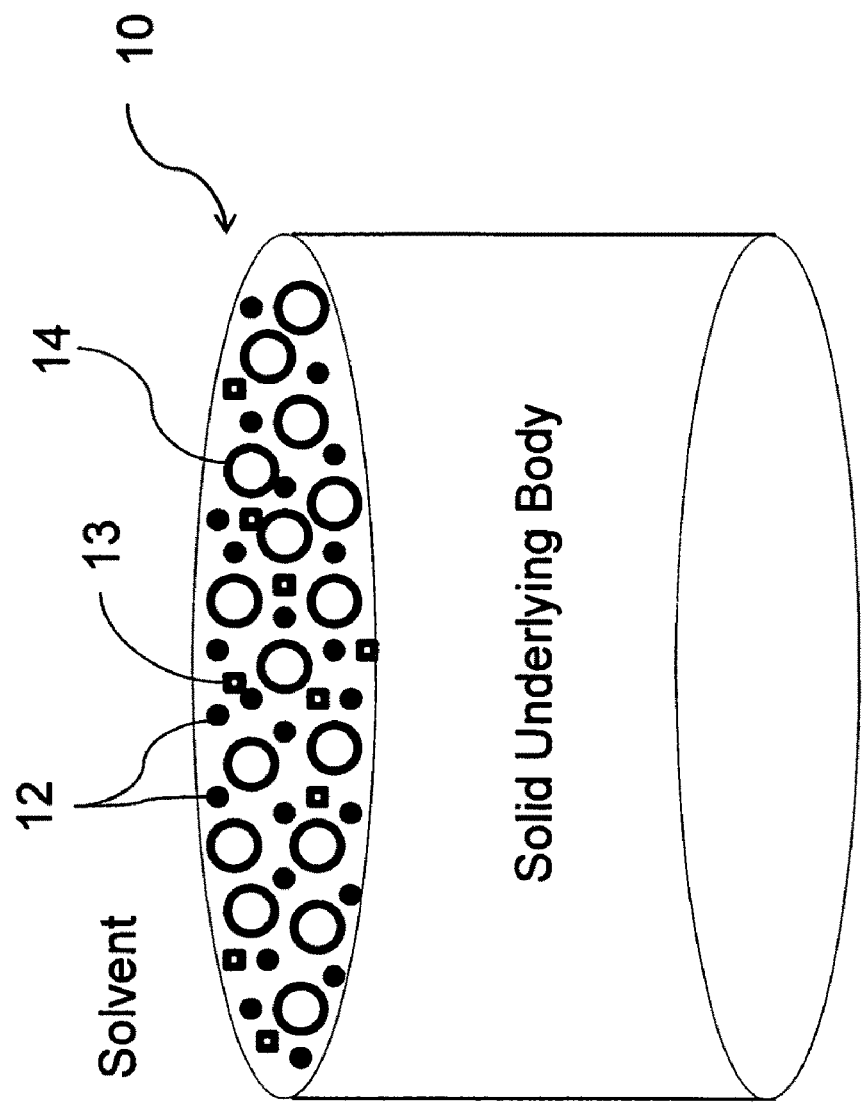
FIG. 3 is the reactor of FIG. 1 after the reactant concentrations inside the activated reaction chambers have reached the depletion level.

FIG. 3 is an exemplary embodiment of reactor 10 in accordance with an embodiment of the invention. Although the reactor 10 in this exemplary embodiment is cylindrically shaped, the invention is not so limited. The reactor 10 is an aggregate composition containing one or more reactants 12, and gelling agent 13, and a chlorite donor encapsulated with a gel-forming material 14. Although the reactants 12, gelling agent 13, and the chlorite donor encapsulated with a gel-forming material 14 are shown only for a solvent interface 16 of the reactor 10, they are preferably present throughout the reactor 10. The gel-forming material of 14 and gelling agent forms a gel when it comes in contact with the main solvent. Thus, when the reactor 10 is placed in contact with the main solvent, the gelling agent in the parts of the reactor 10 that come in contact with the main solvent will form viscous gel that entraps the reactants 12, and divide the wet parts of the reactor 10 into multiple reactor chambers. The gel functions as a membrane allowing some permeation of the main solvent and other fluids across it, but in a restricted manner. Although only one interface 16 is shown in this example for simplicity of illustration, there may be multiple interfaces between the reactor 10 and the main solvent; in fact, the reactor 10 may be placed in a bulk body of main solvent thereby resulting in complete immersion.

Figure 4:
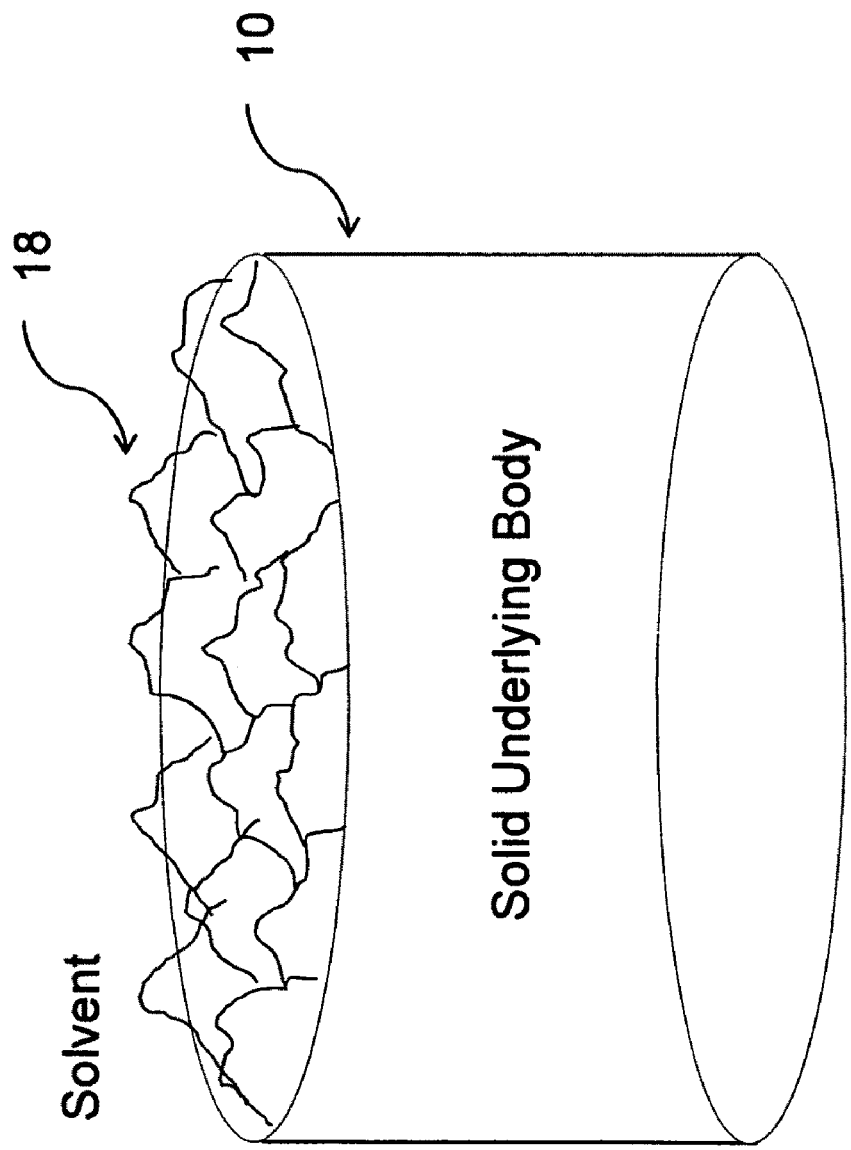
FIG. 4 shows the changes at the solvent interface for a first embodiment of the reactor made with a gelling agent.

FIG. 4 is the reactor 10 after the solvent interface 16 has been exposed to the main solvent. As shown, gel 18 is formed at the interface between the main solvent and the reactor 10. The gel 18, which forms reaction chambers at the interface 16, restricts the diffusion of fluids across it. Thus, the environment inside of the reaction chambers is different from the bulk main solvent body outside the reactor 10. The environment inside the reactor 10 is more conducive to efficient chlorine dioxide generation than the bulk main solvent environment. While the gel walls form in parts of the reactor 10 that is in contact with the main solvent, the dry parts of the reactor 10 remain substantially in their original form.

Figure 5:
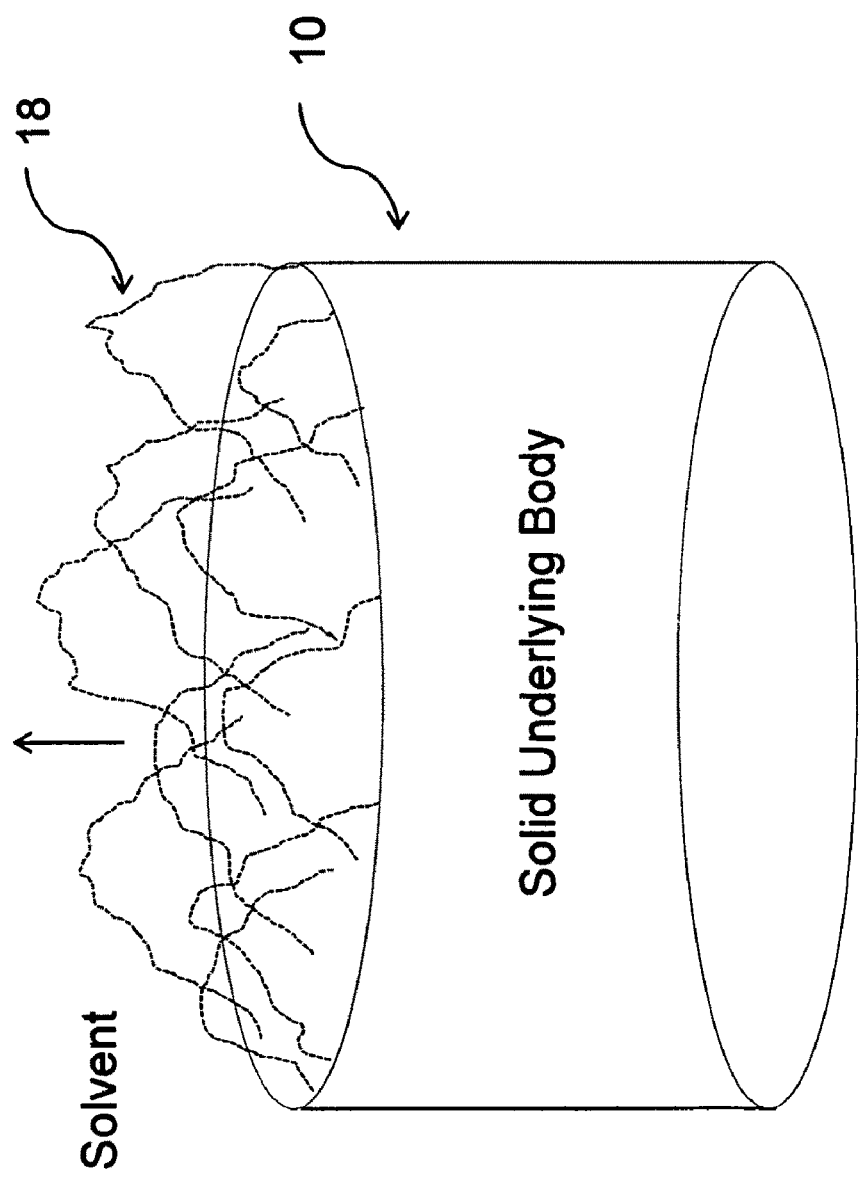
FIG. 5 shows the changes at the solvent interface for a second embodiment of the reactor made with a binder.

FIG. 5 is the reactor 10 after the reactant concentrations inside the activated reaction chambers have reached the depletion level. When the depletion level is reached, the gel walls 18 that form the reaction chambers begin to dissipate or disintegrate, as shown with dotted lines to indicate the dissipation of the colloidal gel. Since the gel walls restricts the main solvent from contacting the deeper portions of the reactor 10, remain substantially dry while the first layer of gel reaction chambers are generating the chlorine dioxide. The dissipation of the gel walls 18, however, causes the layer of reactants and gel-forming material and/or gelling agent that was under the gel layer to come in contact with the main solvent. This newly exposed part of the reactor 10 then contacts the main solvent, forms another set of gel walls, generates the chlorine dioxide, and releases the chlorine dioxide. The next level of reactants-and-gelling agent then comes in contact with the main solvent, and the generation and release of the chlorine dioxide continues as layers of the reactor 10 are dissipated into the main solvent body.

The invention includes a method of preparing the reactor. The reactor produces high concentrations of chlorine dioxide that is different from the reactants that are initially present in the reactor. The method of the invention allows the production of compositions that are stable for storage and, upon activation by contact with water, produce chlorine dioxide in an elevated weight percent yield.

One method for preparing the reactor 10 entails: encapsulating the chlorite donor with a gel-forming material; mixing the encapsulated chlorite donor with reactants and optional gelling agents, fillers, lubricant and the like; and feeding the mixture to agglomerating equipment. Once fed to the agglomerating equipment, a force is applied. The pressure results in the formation of a solid tablet composition. The exact force to be applied is determined based on the final composition, the desired density of the resulting agglomerate, the desired dissolution rates, and the like.

Examples of equipment suitable for producing the solid composition in the form of a tablet may include but may not be limited to: roll compactors; tablet presses; agglomerator; briquetting machines and the like. Suitable equipment is obtainable thru a large number of companies exemplified by GEA Process Engineering Inc, Columbia, Md. 21045, and SMI Incorporated, Lebanon, N.J. 08833.

Figure 6:
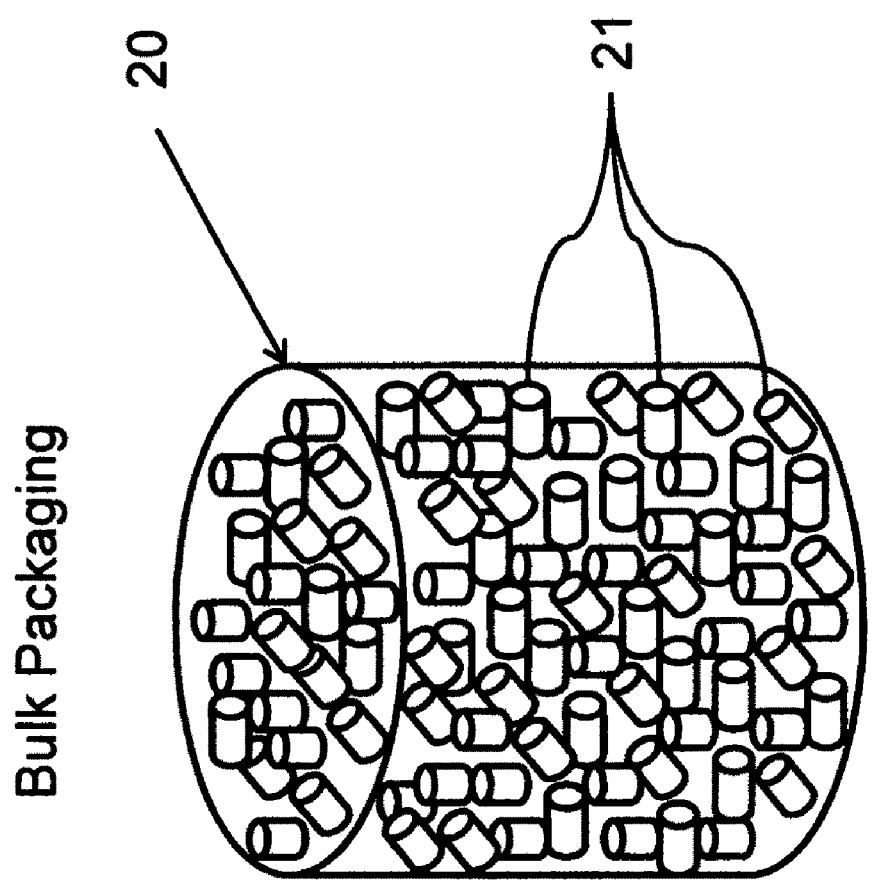
FIG. 6 exemplifies bulk packaging comprising a package such as a pail containing a plurality of tablets comprising the composition.

FIG. 6 is exemplary of bulk packaging but is not intended to limit the types of packaging, multiple layers of packaging that can be implemented to reduce damage to the solid tablet composition, or solid tablet configuration. Additional layers of packaging may include but not limited to: plastic liners; inclusion of desiccant packets such as silica based desiccant; and gas purging of the package such as nitrogen gas purging. Illustration 20 represents a container or packaging into which the solid tablets 21 are contained. A lid or enclosure, more preferably a sealable lid or enclosure is used to reduce the potential for exposure to the external environment.

Gelling Agent

Gelling agents are combined with the reactants to form a mixture. Gelling agents, upon exposure to the main solvent, form a gel that is permeable to the main solvent. Examples of gelling agents include but are not limited to: polysaccharides including cellulose; water absorbent polyacrylic polymers and copolymers such as Carbopol® sold by Noveon, Inc.; poloxamer block copolymer such as Poloxamer 407 sold by BASF under the trade name Pluronic®; polyvinyl alcohol sold under the trade name "Elvanol" by DuPont; poly(ethylene oxide) such as Polyox™ sold by Dow Chemical, can be used. Gelling agents can be a stand-alone polymer as illustrated or a combination of components that may include a stiffening agent or cross-linking agent that slow the dissolution rate of the tablet and/or increase viscosity.

Gelling agents comprise at least one gel-forming polymer. The gel-forming polymer can be natural, such as a gum (e.g. Xanthun gum), semisynthetic such as a polysaccharide (e.g. cellulose derivative), or synthetic such as a poloxamer (block co-polymer of polyoxyethylene and polyoxypropylene), carbomer (crosslinked polymer of acrylic acid), poly (ethylene oxide) and polyvinyl alcohol. The preferred gel-forming polymers are synthetic, as synthetic polymers exemplified by polyvinyl alcohol and ethylene modified copolymer sold under the trade name Exceval® and manufactured by Kuraray Specialties Europe demonstrate high levels of oxidation resistance. However, natural and semisynthetic polymers may be used especially as an additional gel-forming polymer, or in cases where the oxidizers are precoated with a barrier film, such as fumed silica, magnesium carbonate light, borates, and the like.

B. Gelatinous Structure

A tablet may be prepared with a gel-forming material that forms a gelatinous structure when exposed to the main solvent. When the gelatinous structure is formed, so do chambers as described above. The chambers contain reactants that produce the target product from an in-situ chemical reaction, allowing for substantially higher yields of product than tablets having equivalent mass with no gel-forming additive. The gelatinous structure may disintegrate and dissipate after the chamber contents are depleted. The gelatinous structure functions as a membrane.

Using the gelatinous structure of the invention, water-soluble compositions for generating chlorine dioxide can be produced that yield concentrations of chlorine dioxide over 250% more than the existing water-soluble compositions. Further still, the disclosed invention increases the weight percent yield of chlorine dioxide to at least 20 wt % as illustrated in the data section of this disclosure and can achieve in excess of 30 weight percent yield of chlorine dioxide. A tablet composition capable of generation a weight percent yield of at least 20 wt % of chlorine dioxide is unprecedented. Furthermore, the gel-forming materials allow for a tablet composition with substantially improved environmental stability. These characteristics can allow for packaging in bulk by combining multiple tablets in one package. Further still, the use of a gel-forming material provides for a delayed effect that requires a period of elapsed time before any reaction occurs. This characteristic also allows for the controlled release of the chlorine dioxide allowing for use in a multi-tablet dispenser. Water-soluble gels provide superior weight percent yield and improved utility over the existing compositions that utilize high concentrations of inert materials (e.g., swelling clays) to construct a porous structure.

Gel forming additive technology can be readily assimilated into other in-situ generating tablets to achieve the same benefits in yield by increasing the weight % of reactants in the agglomerate composition, and resulting in an increase in the weight % yield of desired product.

The invention is based on the use of gel-forming material that bind and hold the reactants together while immersed in the main solvent, thereby maintaining the structural integrity of the agglomerate composition. The gel, which is formed when the gel-forming material contacts the main solvent, restricts the diffusion of the reactants until the reaction is near complete. After the reaction is substantially complete, the gel disintegrates.

The gel-forming materials are particularly useful in producing self-sustaining tablets that produce high yields of in-situ generated oxidants. The use of this gel-forming technology dramatically reduces the quantity of inert materials used to improve reaction kinetics in prior art, and substantially increases the "weight % yield" of the tablet when compared to tablets incorporating currently known methods.

Without limiting the invention, useful components used in forming water-soluble gels include: natural, semi-synthetic and synthetic polymers such as Polyvinyl alcohol (PVA) or cross-linked polyacrylates sold under the trade name Carbopol® by Novean, and copolymers such as polyoxyethylene polyoxypropylene block copolymer sold under the trade name Pluronic® by BASF, poly (ethylene oxide) exemplified by Polyox sold by Dow chemical, polysaccharides, gums, and water soluble cross-linking agents such as borax in the case of PVA.

Composite gels are particularly useful in that small quantities relative to the total mass of the agglomerate composition dramatically improve the structural integrity of the agglomerate when immersed in water, and improve the weight % yield of the agglomerate composition. Composite gels contain at least two additives that, when combined, produce a gelatinous structure having a viscosity substantially higher than that obtained using either the additive alone when exposed to the same temperature an pH conditions. Composite gels are produced by combining a viscosity-increasing material with an additive that enhances the formation and rigidity of the gel. For example, a composite gel may be a combination of PVA and borax. When composite gelling agents are used, the number and types of compounds that can be used increases. Also, the amount of viscosity modifying agent can often be substantially decreased.

For example, while PVA increases the viscosity of the solution, it has limited effect on the dissolving rate of the tablet at normal use concentrations. Elvanol® sold by DuPont typically shows a viscosity profile of up to approximately 2,000 centipoise at a 10 wt. % solution. However, combining borax or boric acid with an alkali and the PVA produces a gelatinous composite having a viscosity over 100,000 centipoise. Composites can also be produced by combining multiple gel-forming materials to produce a gel of substantially higher viscosity than when the compounds are used with pH buffers as illustrated in the examples.

Gelatinous Structure

In the gelatinous structure capable of producing in-situ generated oxidants in high yield, the viscosity of the gel is sufficiently high to prevent diffusion of the reactants and gel even under conditions that would normally induce rapid dilution. The viscosity being sufficiently high also helps maintain the structural integrity of the agglomerate as to prevent a premature breakup of the agglomerate composition when immersed in excess diluting solvent. The gel rigidity is preferably at a level that is sufficient to prevent rapid dispersion of the agglomerate even when agitation or circulation of the water occurs. To achieve this, it is desirable to utilize a gel-forming chemistry that produces a "gelatinous structure" within the agglomerate. This gelatinous structure has a viscosity greater than about 500 centipose, preferably greater than about 5,000 centipoise, and preferably greater than about 50,000 centipoise. The level of viscosity can be altered to achieve the desired dissolving rate of the tablet.

The gelling agent constitutes no more than 30 wt % of the solid composition, preferably constitutes less than about 10 wt % of the solid composition.

Advantages to Combining Gel-Forming Agents

High solubility reactants such as sodium chlorite and succinic acid when combined with TCCA results in a tablet that when combined with water forms large pores, caverns, and tends to release the high solubility reactants faster than the slower dissolving TCCA. The channels that form can still allow good conversion of chlorite to chlorine dioxide however they compromise the structural integrity of the tablet, thereby making it brittle and crumble under the weight of other tablets in a multi-tablet dispenser. Furthermore, the mechanism that provides a controlled-release as well as a self-limiting tablet is also compromised. These characteristics are undesirable for tablets that are to be used in a multi-tablet dispenser, but may be satisfactory as single or multiple tablet applications that make a single batch of biocidal solution.

By coating or encapsulating the chlorite donor with a gel-forming agent exemplified by polyvinyl alcohol, the environmental stability is greatly enhanced and it reduces the potential of reaction between the chlorite donor and other reactants during manufacturing and storage. By applying a coating onto the sodium chlorite comprising a mixture of partially hydrolyzed polyvinyl alcohol (exemplified by Elvanol 51-03) with a fully hydrolyzed polyvinyl alcohol (exemplified by Elvanol 71-30), results in a solid composition in the form of a tablet with improved environmental stability and suppressed dissolution rate than when Elvanol 51-03 is used alone. By further including another gel-forming agent such as poly (ethylene oxide) exemplified by Polyox WSR N-750 into the mix of reactants that includes the free halogen donor exemplified by TCCA, the dissolution rate of the tablet is dramatically decreased, and the tablet takes on a self-limiting characteristic that limits the maximum concentration of dissolved reactants and in-situ generated biocidal solution on a multi-tablet dispenser.

Applying the Gelling Agent

The gelling agent can be mixed with the other components prior to forming a tablet or agglomerate. A ribbon mixer, tumbler or any convenient commercially viable means of applying the coating to the reactant(s) may be used. It is preferred the polymer coating is in the form of a powder to effectively coat the chlorite donor. Polymer such as Polyvinyl alcohol (PVA) can be difficult to pulverize. Spray drying a solution of polymer exemplified by PVA results in a micronized powder that enhances the coating of the chlorite donor and when applicable distribution within the tablet.

In another application, the gelling agent can be applied to the surface of the reactant(s) having the higher solubility thereby forming a coating, followed by mixing the coated reactant(s) with the other component(s) that have lower solubility. The coating may be applied by simply mixing the gelling agent and reactant together, or by physically attaching the gel-forming material to the surface of the reactant by using methods such as Magnetically Assisted Impact Coating (MAIC).

In yet another application, the gelling agent is applied to the surface of at least the chlorite donor by spraying a solution of the gelling agent onto a surface of the chlorite donor in a fluid bed coating system followed by drying. A suitable method is exemplified by the Wurster process wherein the solid chlorite donor is suspended in a stream of heated air and a solution of gelling agent is sprayed onto the surface of the chlorite donor where it is then dried in the stream of air thereby encapsulating the chlorite donor.

In another application, the gel-forming polymer exemplified by polyvinyl alcohol can be mixed into a solution of sodium chlorite, after which the mixed solution is dried resulting in a matrix of polyvinyl alcohol and sodium chlorite.

Coated Chlorite with Powdered Polyvinyl Alcohol

Commercial 82% granular sodium chlorite was coated with a mixture comprising 89.8 wt % powder Elvanol 52-22 (polyvinyl alcohol) and 10 wt % Pluronic 127prill (poloxamer) that had been intimately mixed by combining the components in a coffee grinder and grinding until a homogenous mix resulted. Then 0.2 wt % of Neobor Tech Powder obtained from U.S. Borax Inc. and mixed in to complete the gelling agent composition.

Granular sodium chlorite was dried at 50° C. for 2 hours and removed from the drier. While still warm, the sodium chlorite granules where combined with the gelling agent and extensively mixed to provide 4 wt % of coating. The coated sodium chlorite was allowed to cool and rest for approximately 2 hours by placing into a container containing silica desiccant and covered.

A batch of components was produced by combining 56 wt % coated sodium chlorite (52 wt % commercial sodium chlorite), 12 wt % succinic acid, 32 wt % TCCA and mixing extensively until uniform.

3 tablets each weighing approximately 3 grams were produced using a Carver tablet press using the methods previously disclosed.

Enhanced Weight Percent Yield and Environmental Stability

3—tablets were exposed to room conditions and tested in one week increments. None of the tablets showed any sign of gas generation during the exposure period. Each tablet was tested by adding to a plastic bucket 17.5 liters of tap water. One tablet was dropped into the center of the bucket and allowed to settle. The bucket was then closed by placing a sealable lid on top and sealing. The bucket was allowed to rest undisturbed for 24 hours. After 24 hours the lid was removed, the water was swirled to disperse the chlorine dioxide rich solution which accumulated in the bottom portion of the water. A sample was removed and the chlorine dioxide concentration was determined using a HACH DR 2000 spectrophotometer.

| Week | wt | ClO2 | wt % Yield | % Conversion |
|------|-----|----------|------------|--------------|
| 1 | 3.0 | 51.6 ppm | 30.1 | 95.4 |
| 2 | 2.9 | 49.0 ppm | 29.5 | 93.7 |
| 3 | 2.9 | 49.5 ppm | 29.9 | 94.7 |

Enhanced Stability with 4 wt % and 10 wt % PVA Coating

| Sample | Date | tablet (g) | sodium chlorite wt % | water (L) | max ClO2 (g) | chlorine dioxide conc ppm | grams | wt % | conversion % |
|---|---|---|---|---|---|---|---|---|---|
| A | 6-May | 1.524 | 0.608 | 1 | 0.509 | 511 | 0.511 | 33.5 | 100 |
| B | 6-May | 1.528 | 0.608 | 1 | 0.51 | 520 | 0.52 | 34 | 101 |
| C | 7-May | 1.63 | 0.608 | 1 | 0.533 | 541 | 0.541 | 33.2 | 101 |
| D | 7-May | 1.513 | 0.608 | 1 | 0.495 | 507 | 0.507 | 33.5 | 102 |
| E | 29-Apr | 1.561 | 0.6 | 1 | 0.548 | 561 | 0.561 | 36 | 102 |
| F | 29-Apr | 1.575 | 0.6 | 1 | 0.553 | 573 | 0.573 | 36 | 103 |
| G | 29-Apr | 1.49 | 0.6 | 1 | 0.524 | 534 | 0.534 | 36 | 101 |

| | | | |
|---|---|---|---|
| A/B | SC (10% PVA) 0.62 | TCCA 0.23 | FCWS 0.17 |
| C/D | SC (10% PVA + 2% MC) 0.62 | 0.23 | 0.17 |
| E/F/G | SC (4% PVA) 0.6 | 0.23 | 0.17 |

Encapsulated Chlorite Using Wurster

Four Kilograms of commercially available granular sodium chlorite reported as 82% sodium chlorite was sent to Aveka, Inc. along with a sample of Elvanol 51-03 (polyvinyl alcohol or PVA).

Aveka, Inc first tested a mixture comprising 96 wt % sodium chlorite and 4 wt % Elvanol 51-03 using thermogravimetric analyses (TGA). The test was conducted up to 200° C. and showed that the oxidation resistant polymer (polyvinyl alcohol) and sodium chlorite had no reaction.

Aveka used a Wurster coater (Vector FL-M-1 unit) to apply a solution of Elvanol 51-03 to the fluidized granular sodium chlorite. Two samples of encapsulated sodium chlorite were produced. One sample had 2 wt % of Elvanol 51-03 applied while the other sample had 4 wt %. The wt % is estimated based on the amount of Elvanol 51-03 applied to the sodium chlorite and assumes all of the Elvanol 51-03 was effectively applied to the fluidized sodium chlorite.

10.84 grams of 4 wt % PVA coated sodium chlorite and 2.4 grams of succinic acid with a particle size of <425 micron was combined and mixed. 0.27 grams of Carbopol 676 was added to the mixture and thoroughly mixed to coat both the PVA-sodium chlorite and succinic acid. 1.2 grams of Polyox WSR N-750 was added and mixed. 6.4 grams of Trichloroisocyanuric acid having a particle size of <180 micron was added and the composition was thoroughly mixed.

Three tablets were produced by adding 5 grams of the mixture to a 16 mm die and pressed using a Carver Laboratory Press using 10,000 lbs of force resulting in a tablet having a cylindrical shape.

Self-Limiting Solid Composition in Tablet Form

One tablet weighing 5.00 grams was added to 25 ml glass vial with a plastic screw on cap. Water was added until the vessel was completely filled. A piece of plastic wrap was applied over the top and the vessel was sealed with the cap. The closed vessel was immersed into a two gallon pail of water for safety purposes.

The tablet was allowed to sit undisturbed for 24 hours. After 24 hours the vessel was held underwater and the lid was removed, and the contents containing a thick viscous solution of bright yellow chlorine dioxide where spilled out. The chunk of remaining tablet was removed, rinsed to remove loose gel, and dried with a paper towel. The sample weight was 1.77 grams.

Another tablet was added to 1000 ml of water and the beaker was covered with plastic wrap. The tablet was completely dissolved in 11 hours 45 minutes.

Delayed Reaction

Another 5 gram tablet was dropped into 3500 ml of 80° F. water. The tablet landed on the bottom and required an additional 5 seconds before any indication of chlorine dioxide formation was detected. Subsequent test utilizing a 10 wt % PVA coating of chlorite provided 10 seconds of delay before the generation of chlorine dioxide was observed.

Enhanced Weight Percent Yield

Three tablet compositions for each of three different water soluble formulations were produced. The chlorite was encapsulated with 4 wt % PVA. The ratios of components were as follows:

| | Formula 1 | Formula 2 | Formula 3 |
|---|---|---|---|
| | chlorite 0.54 g | chlorite 0.6 | chlorite 0.54 |
| | TCCA .0.32 g | TCCA 0.2 | TCCA 0.30 |
| | fumaric 0.14 g | fumaric 0.2 | fumaric 0.16 |

| | tablet (g) | sodium chlorite wt % | moles | water (L) | chlorine dioxide conc ppm | grams | moles | conversion % |
|---|---|---|---|---|---|---|---|---|
| Formula 1 | 5.129 | 54 | 0.02523 | 2 | 845 | 1.69 | 0.02522 | 100 |
| | 5.03 | 54 | 0.0247 | 6 | 273 | 1.638 | 0.0244 | 100 |
| | 9.658 | 54 | 0.0475 | 8 | 395 | 3.16 | 0.04716 | 100 |
| Formula 2 | 4.987 | 60 | 0.02726 | 3 | 519 | 1.557 | 0.02323 | 89.2 |
| | 4.996 | 60 | 0.027311 | 2 | 839 | 1.678 | 0.02504 | 96.1 |
| Formula 3 | 5.06 | 54 | 0.02489 | 3 | 545 | 1.635 | 0.0244 | 98 |
| | 5.07 | 54 | 0.0249 | 2 | 837 | 1.674 | 0.0249 | 100 |

The non-hygroscopic fumaric acid made a very environmentally stable tablet compared to the succinic acid. Formula 2 illustrates a tablet composition with excess chlorite that would deplete virtually all of the free chlorine, thereby resulting in an antimicrobial solution with very little potential for generating trihalomethanes when used in food processing applications. The sodium chlorite provides a minimum 82 wt % sodium chlorite. In cases where the calculated chlorine dioxide was greater than 100 wt %, the discrepancy may be attributed to a higher activity of chlorite in the commercial product than that reported as the minimum on the label.

Chlorite Limits for Achieving 70% Conversion

|  | tablet (g) | wt % | water (L) | max ClO2 (g) | conc ppm | grams | conversion % |
|---|---|---|---|---|---|---|---|
| Formula A | 1.511 | 61 | 1 | 0.5401 | 516 | 0.516 | 95.5 |
|  | 1.512 | 61 | 2 | 0.5405 | 510 | 0.51 | 94.3 |
|  | 4.99 | 61 | 2 | 1.7837 | 822 | 1.644 | 92.17 |
| Formula B | 1.5 | 65 | 2 | 0.5713 | 256 | 0.512 | 89.6 |
|  | 1.5 | 65 | 1 | 0.5713 | 505 | 0.505 | 88.39 |
|  | 1.506 | 65 | 1 | 0.5736 | 509 | 0.509 | 88.73 |
|  | 1.501 | 65 | 1 | 0.5717 | 500 | 0.5 | 87.4 |
| Formula C | 4.97 | 70 | 2 | 2.0386 | 685 | 1.37 | 67.2 |
|  | 1.497 | 70 | 1 | 0.614 | 437 | 0.437 | 71.1 |
| Formula D | 1.521 | 61.9 | 1 | 0.5406 | 536 | 0.536 | 99.1 |
|  | 1.491 | 61.9 | 2 | 0.53 | 257 | 0.514 | 96.9 |
|  | 1.515 | 61.9 | 3 | 0.5385 | 176 | 0.528 | 98 |
|  | 5.048 | 61.9 | 6 | 1.794 | 281 | 1.686 | 94 |
|  | 5.012 | 61.9 | 8 | 1.782 | 213 | 1.704 | 95.6 |
|  | 2.002 | 61.9 | 0.8 | 0.7116 | 851 | 0.68 | 95.5 |

|  | SC (4% pva) | TCCA | FCWS | Polyox |
|---|---|---|---|---|
| Formula A | 0.61 | 0.22 | 0.14 | 0.03 |
| Formula B | 0.65 | 0.2 | 0.13 | 0.02 |
| Formula C | 0.7 | 0.25 | 0.05 |  |
| Formula D** | 0.6 | 0.2 | 0.17 |  |

|  | tablet (g) | sodium chlorite wt % | water (L) | max SC (gm) | max ClO2 (gm) | max ClO2 mg/ltr | ClO2 ppm | wt % | Conversion % |
|---|---|---|---|---|---|---|---|---|---|
| Formula B | 1.517 | 72 | 8 | 1.0486 | 0.6363 | 79.53 | 54 | 28.4 | 67.9 |
|  | 1.549 | 72 | 3.5 | 1.0707 | 0.6497 | 185.63 | 132 | 29.8 | 71.11 |
|  | 1.52 | 72 | 2 | 1.0506 | 0.6375 | 318.75 | 221 | 29.1 | 69.33 |
|  | 1.527 | 72 | 1 | 1.0555 | 0.6405 | 640.48 | 463 | 30.3 | 72.29 |

|  | NaClO2 4% PVA | TCCA | Fumaric |
|---|---|---|---|
| Formula B | 0.72 | 0.2 | 0.08 |

**used 2% MgCO3.

These sets of data show the range limits, enhances weight percent yield, and various conversions of chlorite anion to chlorine dioxide for various tablet formulations using Trichloroisocyanuric acid (TCCA), Sodium Chlorite (SC), and Fumaric acid, (FCWS).

The disinfection requirements of an open recirculating industrial cooling system are markedly different from those of a potable water treatment facility. The disinfection goal of potable water facilities is the sterilization of water as measured by specific water borne pathogens. The goal of disinfection for industrial cooling systems is the removal or minimization of any biofilm, which retards heat transfer, causes biofouling, provides a place of agglomeration for marginally soluble or insoluble salts, and provides a place which nurtures and promotes the growth of highly corrosive anaerobic bacteria.

Many researchers have cited the excellent biofilm removing properties of chlorine dioxide. In at least one previously reported case history, the introduction of chlorine dioxide into a heavily fouled cooling system resulted in an increase in both turbidity and calcium. These were explained by a dispersing of the biofilm which both increased turbidity and released small calcium carbonate particulates which had been trapped in the biofilm.

Other industries have made use of the excellent biofilm removal properties of chlorine dioxide, particularly the food industry. Small cooling towers, frequently contaminated by food products or by-products, have tremendous slime forming potential. Chlorine dioxide has achieved widespread usage in such systems, due to its excellent biofilm dispersing/bacterial disinfecting properties.

The composition of the invention is effective as a biocide and algaecide treatment for use in recirculated water systems such as industrial cooling systems and swimming pools. While the foregoing has been with reference to a particular embodiment of the invention, it will be appreciated by those skilled in the art that changes in this embodiment may be made without departing from the principles and spirit of the invention.

What is claimed is:

1. A solid composition in the form of a tablet that produces chlorine dioxide on demand upon contact with water, the composition comprising:
   at least one solid chlorite donor in an amount to provide chlorite anion to obtain at least 25 wt % yield chlorine dioxide when the composition is contacted with water;

at least one solid form of low solubility free halogen donor in an amount from 12 to 60 wt % and in an amount to convert at least 70 wt % of the chlorite anion to chlorine dioxide when the composition is contacted with water;

at least one solid acid source in an amount to provide a pH of less than 7.8 when 1 gram of tablet composition is dissolved in 100 ml of water; and a coating covering the chlorite donor, the coating comprising at least one gel-forming polymer, the coating being present in an amount to provide a yield of chlorine dioxide of at least 25 wt % at a conversion of chlorite anion to chlorine dioxide of at least 70 wt % when the composition is contacted with water, wherein the coating being constructed to provide a gelatinous membrane encapsulating the chlorite donor upon contact with water which slows a dissolution rate of the chlorite donor, creates a chamber in which chlorine dioxide is produced, restricts diffusion of the chlorite donor and chlorine dioxide out of the chamber, and restricts diffusion of water into the chamber, and all wt % being based on the total weight of the composition unless otherwise stated.

2. The composition according to claim 1, wherein the coating is constructed to dissipate when a depletion level is reached inside the chamber.

3. The composition according to claim 1, wherein the gel-forming polymer is present in an amount of 0.1 to 30 wt %.

4. The composition according to claim 1, wherein the gel-forming polymer is present in an amount of 0.5 to 20 wt %.

5. The composition according to claim 1, wherein all of the chlorite donor is coated.

6. The composition according to claim 1, wherein the chlorite donor comprises sodium chlorite.

7. The composition according to claim 1, wherein the chlorite donor and the coating are present in an amount to provide at least 30 wt % yield of chlorine dioxide when the composition is contacted with water.

8. The composition according to claim 1, wherein the free halogen donor comprises trichloroisocyanuric acid.

9. A tablet composition according to claim 1, wherein the gel-forming polymer comprises polyvinyl alcohol.

10. The composition according to claim 1, wherein the gel-forming polymer comprises polyvinyl alcohol and the composition comprises a stiffening agent comprising boron.

11. The composition according to claim 1, wherein the free halogen donor is coated with a coating comprising at least one gel-forming polymer.

12. The composition of claim 1, further comprising a plurality of the tablets contained in a bulk package, wherein the tablets are in intimate contact with one another.

13. The composition of claim 1, further comprising a plurality of the tablets contained in a multi-tablet chemical dispenser.

14. The composition of claim 1, wherein the solid composition in the form of a tablet has enhanced environmental stability.

15. The composition of claim 1, wherein the solid composition in the form of a tablet provides a controlled release of chlorine dioxide when contacted with water.

16. The composition according to claim 1, wherein the acid source comprises at least one acid selected from the group consisting of dicarboxylic acids and tricarboxylic acids.

17. The composition according to claim 1, wherein the acid source comprises fumaric acid.

18. The composition according to claim 1, wherein the acid source comprises tartaric acid.

19. The composition according to claim 1, wherein the acid source comprises citric acid.

20. The composition according to claim 1, wherein the acid source comprises succinic acid.

21. The composition according to claim 1, wherein composition is self-limiting.

22. The composition according to claim 10, wherein the composition comprises an effective amount of combustion suppressing boron donor.

23. The composition according to claim 1, wherein the polymer comprises an oxidation resistance polymer to avoid reacting with the chlorite donor when a mixture of the oxidation resistant polymer and chlorite donor is heated to temperatures to at least 100° C.

24. The composition according to claim 1, wherein the at least the chlorite donor is coated with an anti-caking agent comprising magnesium carbonate.

25. The composition according to claim 1, wherein the at least the chlorite donor is coated with an anti-caking agent comprising fumed silica.

26. A solid composition that produces chlorine dioxide on demand upon contact with water, the composition comprising:

a solid chlorite donor comprising sodium chlorite in an amount to provide at least 25 wt % yield chlorine dioxide when the composition is contacted with water;

a low solubility free halogen donor comprising trichloroisocyanuric acid in an amount from 12 to 60 wt % and in an amount to convert at least 70 wt % of the chlorite anion to chlorine dioxide when the composition is contacted with water;

fumaric acid in an amount to provide a pH of less than 7.8 when 1 gram of tablet composition is dissolved in 100 ml of water; and a coating covering the chlorite donor, the coating comprising polyvinyl alcohol, the coating being present in an amount to provide a yield of chlorine dioxide of at least 25 wt % at a conversion of chlorite anion to chlorine dioxide of at least 70 wt % when the composition is contacted with water, wherein the coating being constructed to provide a gelatinous membrane encapsulating the chlorite donor upon contact with water which slows a dissolution rate of the chlorite donor, creates a chamber in which chlorine dioxide is produced, restricts diffusion of the chlorite donor and chlorine dioxide out of the chamber, and wherein all wt % being based on the total weight of the composition unless otherwise stated.

27. A method of producing chlorine dioxide on demand comprising contacting a solid composition in the form of a tablet with water, the solid composition comprising:

at least one solid chlorite donor in an amount to provide sufficient chlorite anion to obtain at least 25 wt % chlorine dioxide when the composition is contacted with water;

at least one solid form of free halogen donor in an amount from 12 to 60 wt % and in an amount to convert at least 70 wt % of the chlorite anion to chlorine dioxide when the composition is contacted with water;

at least one solid acid source in an amount to provide a pH of less than 7.8 when 1 gram of tablet composition is dissolved in 100 ml of water; and a coating covering at least the chlorite donor, the coating comprising at least one gel-forming polymer, the coating being present in an amount to provide a yield of chlorine dioxide of at least 25 wt % at a conversion of chlorite anion to chlorine dioxide of at least 70 wt % when the composition is contacted with water, wherein the coating being constructed to provide a gelatinous membrane encapsulating the chlorite donor upon contact with water which slows a dissolution rate of the chlorite donor, creates a chamber in which chlorine dioxide is produced, restricts diffusion of the chlorite donor and chlorine dioxide out of the chamber, and restricts diffusion of water into the chamber, and wherein all wt % being based on the total weight of the composition unless otherwise stated.

28. The method according to claim 27, wherein the coating dissipates when a depletion level is reached inside the chamber.

29. The method according to claim 27, wherein the gel-forming polymer is present in an amount of 0.1 to 30 wt %.

30. The method according to claim 27, wherein all of the chlorite donor is coated.

31. The method according to claim 27, wherein the chlorite donor comprises sodium chlorite.

32. The method according to claim 27, wherein the chlorite donor and the coating are present in an amount to provide at least 30 wt % yield of chlorine dioxide when the composition is contacted with water.

33. The method according to claim 27, wherein the free halogen donor comprises trichloroisocyanuric acid.

34. The method according to claim 27, wherein the free halogen donor comprises dichloroisocyanuric acid.

35. The composition according to claim 27, wherein the free halogen donor comprises a low solubility free halogen donor having a solubility of no greater than 5 grams per 100 ml of water at 25° C.

36. The method according to claim 27, wherein the gel-forming polymer comprises polyvinyl alcohol.

37. The method according to claim 27, wherein the gel-forming polymer comprises polyvinyl alcohol and the composition further comprises a stiffening agent comprising boron.

38. The method according to claim 27, wherein the free halogen donor is coated with a coating comprising at least one gel-forming polymer.

39. The method according to claim 27 further comprising a plurality of tablets packaged in bulk wherein the tablets are in intimate contact within the package.

40. The method according to claim 27 further comprising decanting the plurality of the tablets from a bulk package into a multi-tablet chemical dispenser prior to contacting the tablets with the water.

41. The method according to claim 27 further comprising contacting the tablets with the water in the multi-tablet chemical dispenser, resulting in the controlled release of chlorine dioxide.

42. The method according to claim 27, wherein the acid source comprises at least one acid selected from the group consisting of dicarboxylic acids and tricarboxylic acids.

43. The method according to claim 27, wherein the acid source comprises fumaric acid.

44. The method according to claim 27, wherein the acid source comprises tartaric acid.

45. The method according to claim 27, wherein the acid source comprises citric acid.

46. The method according to claim 27, wherein the acid source comprises succinic acid.

47. The method according to claim 27, further comprising using the chlorine dioxide produced as an antimicrobial agent.

48. The method according to claim 27, further comprising using the chlorine dioxide produced for the treatment of food processing applications.

49. The method according to claim 27, further comprising using the chlorine dioxide produced for the treatment of recirculating systems.

50. The method according to claim 27, further comprising using the chlorine dioxide produced for the treatment of hard surfaces.

51. The method according to claim 27, further comprising using the chlorine dioxide produced for the treatment of emergency drinking water.

52. The method according to claim 27, further comprising using the chlorine dioxide produced for the treatment of surgical instruments and equipment.

53. The method according to claim 27, further comprising adjusting the rate of formation of chlorine dioxide by adjusting the amount of coating present on the chlorite donor.

54. The method according to claim 27, wherein composition is self-limiting such that when the concentration of chlorine dioxide and composition components reach a saturation level the generation of chlorine dioxide ceases.

55. The method according to claim 27, wherein the polymer has sufficient oxidation resistance to avoid reacting with the chlorite donor when a mixture of oxidation resistant polymer and chlorite donor is heated to temperatures to at least 100° C.

56. The method according to claim 37, wherein the composition comprises an effective amount of combustion suppressing boron donor.

57. The method according to claim 27, wherein the at least the chlorite donor is coated with an anti-caking agent comprising magnesium carbonate.

58. The method according to claim 27, wherein the at least the chlorite donor is coated with an anti-caking agent comprising fumed silica.

* * * * *